(12) United States Patent
Atanasoska et al.

(10) Patent No.: US 7,850,645 B2
(45) Date of Patent: Dec. 14, 2010

(54) INTERNAL MEDICAL DEVICES FOR DELIVERY OF THERAPEUTIC AGENT IN CONJUNCTION WITH A SOURCE OF ELECTRICAL POWER

(75) Inventors: Liliana Atanasoska, Edina, MN (US); Thomas J. Holman, Princeton, MN (US); Jan Weber, Maple Grove, MN (US); Robert Warner, Woodbury, MN (US); Scott Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1618 days.

(21) Appl. No.: 11/055,930

(22) Filed: Feb. 11, 2005

(65) Prior Publication Data
US 2006/0184092 A1    Aug. 17, 2006

(51) Int. Cl.
*A61M 29/00*    (2006.01)
(52) U.S. Cl. .................. 604/96.01; 604/500; 604/501; 604/502; 604/98.01; 604/101.01; 604/101.05; 604/103; 604/103.01; 604/104; 604/20
(58) Field of Classification Search .......... 604/20, 604/500–502, 96.01–103, 103.01–104
See application file for complete search history.

(56) References Cited

U.S. PATENT DOCUMENTS 5,019,034 A    5/1991    Weaver et al. ............ 604/20
(Continued)

FOREIGN PATENT DOCUMENTS
WO    WO 03/070875 A2    8/2003
WO    WO 2004/105864 A1    12/2004

OTHER PUBLICATIONS

Biswas, Mukul, and Anindita Roy. "Chemical modification of polypyrrole. II. Thermal stability, dielectric, and conductivity characteristics of polypyrrole substituted with phthalic and pyromellitic dianhydride." Journal of Applied Polymer Science 54 (1994): 1483-489.*

(Continued)

*Primary Examiner*—Nicholas D Lucchesi
*Assistant Examiner*—Scott Medway
(74) *Attorney, Agent, or Firm*—Mayer & William; David B. Bonham; Keum J. Park

(57) ABSTRACT

The invention generally relates to internal (e.g., implantable, insertable, etc.) drug delivery devices which contain the following: (a) one or more sources of one or more therapeutic agents; (b) one or more first electrodes, (c) one or more second electrodes and (d) one or more power sources for applying voltages across the first and second electrodes. The power sources may be adapted, for example, to promote electrically assisted therapeutic agent delivery within a subject, including electroporation and/or iontophoresis. In one aspect of the invention, the first and second electrodes are adapted to have tissue of a subject positioned between them upon deployment of the medical device within the subject, such that an electric field may be generated, which is directed into the tissue. Furthermore, the therapeutic agent sources are adapted to introduce the therapeutic agents into the electric field. In another aspect, the therapeutic agent sources are polymeric regions that contain one or more types of ion-conductive polymers and one or more types of charged therapeutic agents. In yet another aspect, the therapeutic agent sources are polymeric regions that contain one or more types of electrically conductive polymers and one or more types of charged therapeutic agents.

42 Claims, 15 Drawing Sheets

U.S. PATENT DOCUMENTS

| | | | |
|---|---|---|---|
| 5,087,787 A * | 2/1992 | Kimble et al. | 585/500 |
| 5,282,785 A * | 2/1994 | Shapland et al. | 604/21 |
| 5,304,120 A | 4/1994 | Crandell et al. | 604/52 |
| 5,318,514 A * | 6/1994 | Hofmann | 604/20 |
| 5,419,767 A * | 5/1995 | Eggers et al. | 604/114 |
| 5,507,724 A | 4/1996 | Hofmann et al. | 604/53 |
| 5,556,383 A | 9/1996 | Wang et al. | 604/96 |
| 5,704,908 A | 1/1998 | Hofmann et al. | 604/21 |
| 5,749,845 A | 5/1998 | Hildebrand et al. | 604/21 |
| 5,807,306 A | 9/1998 | Shapland et al. | 604/21 |
| 5,938,659 A * | 8/1999 | Tu et al. | 606/41 |
| 5,944,710 A | 8/1999 | Dev et al. | 604/500 |
| 6,096,000 A * | 8/2000 | Tachibana et al. | 604/20 |
| 6,197,013 B1 * | 3/2001 | Reed et al. | 604/509 |
| 6,210,392 B1 | 4/2001 | Vigil et al. | 604/507 |
| 6,219,577 B1 | 4/2001 | Brown, III et al. | 604/20 |
| 6,233,482 B1 | 5/2001 | Hofmann et al. | 604/21 |
| 6,241,701 B1 | 6/2001 | Hofmann | 604/21 |
| 6,280,411 B1 | 8/2001 | Lennox | 604/103.05 |
| 6,300,108 B1 | 10/2001 | Rubinsky et al. | 435/173.6 |
| 6,468,304 B1 | 10/2002 | Dubois-Rande et al. | 623/1.42 |
| 6,562,604 B2 | 5/2003 | Rubinsky et al. | 435/173.6 |
| 6,603,998 B1 * | 8/2003 | King et al. | 604/20 |
| 6,625,486 B2 | 9/2003 | Lundkvist et al. | 604/21 |
| 6,685,648 B2 | 2/2004 | Flaherty et al. | 600/464 |
| 6,692,456 B1 | 2/2004 | Eppstein et al. | 604/22 |
| 6,714,816 B1 | 3/2004 | Heller et al. | 607/3 |
| 6,723,814 B2 * | 4/2004 | Meier et al. | 526/279 |
| 6,730,699 B2 | 5/2004 | Li et al. | 514/449 |
| 6,735,471 B2 * | 5/2004 | Hill et al. | 607/2 |
| 6,810,286 B2 | 10/2004 | Donovan et al. | 607/2 |
| 6,972,013 B1 * | 12/2005 | Zhang et al. | 604/501 |
| 7,037,562 B2 * | 5/2006 | Jimenez | 428/36.4 |
| 7,470,252 B2 * | 12/2008 | Mickley et al. | 604/103.02 |
| 2001/0007666 A1 | 7/2001 | Hoffman et al. | 424/400 |
| 2002/0022795 A1 | 2/2002 | Reynolds et al. | 604/20 |
| 2002/0022826 A1 | 2/2002 | Reynolds et al. | 604/890.1 |
| 2002/0035346 A1 | 3/2002 | Reynolds et al. | 604/20 |
| 2003/0083645 A1 | 5/2003 | Angel et al. | 604/890.1 |
| 2003/0204206 A1 | 10/2003 | Padua et al. | 607/2 |
| 2003/0206910 A1 | 11/2003 | Nicol et al. | 424/178.1 |
| 2003/0236514 A1 | 12/2003 | Schwarz | 604/890.1 |
| 2004/0002747 A1 * | 1/2004 | Ryan et al. | 607/101 |
| 2004/0044308 A1 * | 3/2004 | Naimark et al. | 604/103 |
| 2004/0106841 A1 | 6/2004 | Shaw et al. | 600/3 |
| 2004/0219660 A1 | 11/2004 | Dev et al. | 435/285.2 |
| 2005/0043680 A1 * | 2/2005 | Segal et al. | 604/104 |

OTHER PUBLICATIONS

Directions to Kensey Nash, Angio-Seal® Device. http://www.kenseynash.com/corp/angio_diagram.htm, 2 pages, precise date unknown, but prior to the filing date of the present application. Downloaded Jun. 15, 2005.

"Cardiac Catheterisation", http://www.fleshandbones.com/readingroom/pdf/971.pdf, 4 pages, precise date unknown, but prior to the filing date of the present application.

Sahota TS, et. al., "In Vitro Iontophoretic Release of Lithium Chloride and Lidocaine Hydrochloride from Polymer Electrolytes", Drug Development and Industrial Pharmacy, Oct. 2000, vol. 26 (10), pp. 1039-1044. http://www.ncbi.nlm.nih.gov/entrez/query.fcgi?cmd=Retrieve&db=PubMed&list_uids=11, 1 page. Abstract.

Murdan S., "Electro-Responsive Drug Delivery from Hydrogels", Department of Pharmaceutics, The School of Pharmacy, University of London, Sep. 19, 2003, vol. 92 (1-2):1-17. http://www.ncbi.nlm.nih.gov/entrez/query.fcgi?cmd=Retrieve&db=PubMed&list_uids=14, 2 pages. Abstract.

Cullen T. Vogelson, "Advances in Drug Delivery Systems", Modern Drug Discovery, from concept to Development, http://pubs.acs.org/subscribe/journals/mdd/v04/i04/html/MDD04FeatureVogelson.html, Apr. 2001, vol. 4, No. 4, pp. 49-50, 52.

Sahota TS, et. al., "Physical Characterization of Polymer Electrolyte Iontophoretic Drug Delivery Devices", Drug Development and Industrial Pharmacy, Mar. 1999, vol. 25, (3), pp. 307-313. http://www.ncbi.nlm.nih.gov/entrez/query.fcgi?cmd=Retrieve&db=PubMed&list_uids=10 Abstract.

Sahota TS, et. al., "Physical Characterization of Polymer Electrolytes as Novel Iontophoretic Drug Delivery Devices", Drug Development and Industrial Pharmacy, Mar. 1999, vol. 25, pp. 307-313, http://www.dekker.com/servlet/product/DOI/101081DDC100102175. Abstract.

"Battery", The Pennsylvania State University, http://research.chem.psu.edu/hragroup/battery.htm, 2 pages. Downloaded Jun. 15, 2005.

"Lithium Polymer Batteries", Technology Opportunity, Glenn Research Center, Cleveland, Ohio. http://www.technology.grc.nasa.gov/tops/TOP300163.pdf, May 2004, 2 pages.

W. Kutner, et al., "Analytical Aspects of Chemically Modified Electrodes: Classification, Critical Evaluations and Recommendations" 1998, Pure and Applied Chemistry, vol. 70, No. 6, pp. 1301-1318.

So Yeon Kim, et. al., "Drug Release Behavior of Electrical Responsive Poly(Vinyl Alcohol)/ Poly(Acrylic Acid) IPN Hydrogels Under an Electric Stimulus", Journal of Applied Polymer Science, 1999, vol. 74, pp. 1752-1761.

F. Cunha, et. al., "Iontophoretic Materials", 1 page. Precise date unknown, but prior to the filing date of the present application.

C.R. Dass, et. al., "Apolipoprotein A-I, Phospholipid Vesicles, and Cyclodextrins as Potential Anti-Atherosclerotic Drugs: Delivery, Pharmacokinetics, and Efficacy", Drug Delivery, vol. 7, pp. 161-182.

Electroporation, 1 page. Precise date unknown, but prior to the filing date of the present application.

John P. Dimarco, "Implantable Cardioverter-Defibrillators", The New England Journal of Medicine, vol. 349, Nov. 6, 2003, pp. 1836-1847.

Rainer Gradaus, et. al. "ICD Leads: Design and Chronic Dysfunctions", Feb. 2003, Pace, Part I, vol. 26, pp. 649-657.

Nipon Chattipakorn, MD, et. al. "Locally Propagated Activation Immediately After Internal Defibrillation", Circulation, 1998, vol. 97, pp. 1401-1410.

Joseph F. Mitchel, et. al. "Catheter-Based Local Thrombolysis with Urokinase: Comparative Efficacy of Intraluminal Clot Lysis with Conventional Urokinase Infusion Techniques in an In Vivo Porcine Thrombus Model", Catheterization and Cardiovascular Diagnosis, vol. 41, pp. 293-302 (1997).

Pedro Gomez-Romero, "Hybrid Organic-Inorganic Materials—In Search of Synergic Activity", Advanced Materials, Feb. 5, 2001, vol. 13, No. 3, pp. 163-174.

Fábio A. Beleze, et. al., "Synthesis and Characterization of Organic-Inorganic Hybrids Formed Between Conducting Polymers and Crystalline Antimonic Acid", J. Braz. Chem. Soc., 2001, vol. 12, No. 4 pp. 542-547.

Zhonghua Peng, "Rational Synthesis of Covalently Bonded Organic-Inorganic Hybrids", Angrew. Chem. Int. Ed. 2004, vol. 43, pp. 930-935.

Mark J. MacLachlan, et al., "New (Inter) Faces: Polymers and Inorganic Materials", Advanced Materials, 2000, vol. 12, No. 9, pp. 675-681.

Wuu-Jyl Liang, et. al., "Morphology and Ionic Conductivity Studies of Hybrid Electrolytes Based on Epoxide-Crosslinked Polysiloxane/Polyether Networks", Macromolecular Chemistry and Physics, 2004, vol. 205, pp. 600-610.

Noel Caplice, et. al., "Gene Transfer for Coronary Restenosis", Novel Revascularization Strategies, Current Interventional Cardiology Reports, 1999, vol. 1, pp. 157-164.

Afsaneh Lavasanifar, et. al., "Poly (ethylene Oxide)-Block-Poly (L-Amino Acid) Micelles for Drug Delivery", Advanced Drug Delivery Reviews, 2002, vol. 54, pp. 169-190.

Yoshinori Kakizawa, et. al., "Block Copolymer Micelles for Delivery of Gene and Related Compounds", Advanced Drug Delivery Reviews, 2002, vol. 54, pp. 203-222.

Aldara™ Drug Information, 3M Pharmaceuticals, Jul. 2004, 6 pages.

Leesa J. Deterding, et. al., "Separation and Characterization of Human High-Density Apolipoproteins Using a Nonaqueous Modifier in Capillary Electrophoresis-Mass Spectrometry", Electrophoresis, 2002, vol. 23, pp. 2296-2305.

Victor M. Bolaños-García, et. al. "Monolayers of Apolipoproteins at the Air/Water Interface", J. Phys. Chem. B, 2001, vol. 105, pp. 5757-5765.

Igor L. Radtchenko, et. al. "A Novel Method for Encapsulation of Poorly Water-Soluble Drugs: Precipitation in Polyelectrolyte Multilayer Shells", International Journal of Pharmaceutics, 2002, vol. 242, pp. 219-223.

Tarek A. El-Aguizy, et. al., "Transplanting Carbon Nanotubes", Applied Physics Letters, Dec. 13, 2004, vol. 85, No. 24, pp. 5995-5997.

J. M. Sansiñena, et. al., "A Solid Artificial Muscle Based on Polypyrrole and Solid Polymeric Electrolyte Working in Air", Chem. Commun., 1997, pp. 2217-2218.

Moon Gyu Han, et. al., "X-Ray Photoelectron Spectroscopy Study of Electrically Conducting Polyaniline/Polyimide Blends", Polymer, 2000, vol. 41, pp. 3253-3262.

Benoit Piro, et. al., "Electrochemical Method for Entrapment of Oligonucleotides in Polymer-Coated Electrodes", J. Biomed. Mater. Res., 1999, vol. 46 No. 4, pp. 566-572.

Hua Huang, et. al., "Probe Beam Deflection Study on Electrochemically Controlled Relsease of 5-Fluorouracil", Electrochimica Acta, 1998, vol. 43, No. 9, pp. 999-1004.

Seung-Ki Lee, et. al., "Experimental Analysis on the Properties of Polypyrrole as Drug Delivery System Materials", Smart Structures and Materials 2003: Electroactive Polymer Actuators and Devices (EAPAD), Proceedings of SPIE, vol. 5051 (2003), pp. 338-348.

Ronald L. Blankespoor, et. al., "Polymerized 3-Methoxythiophene. A Processable Material for the Controlled Release of Anions", J. Chem. Soc., Chem. Commun., 1985 pp. 90-92.

An-Cheng Chang, et. al., "Electrochemically Controlled Binding and Release of Salicylate, TCNQ and Ferrocyanide from Films of Oligomeric 3-Methoxythiophene", J. Electroanal. Chem., 1998, vol. 247, pp. 173-184.

Baruch Zinger, et. al., "Timed Release of Chemicals from Polypyrrole Films", J. Am. Chem. Soc., 1984, vol. 106, pp. 6861-6863.

Yali Li, et. al., "Plasma Protein Adsorption and Thrombus Formation on Surface Functionalized Polyprrole With and Without Electrical Stimulation", Journal of Colloid and Interface Science, 2004, vol. 275, pp. 488-495.

Jaber G. Qasem, et. al. "Kinetics of Paclitaxel 2'-N-Methylpyridinium Mesylate Decomposition", AAPS PharmSciTech, 2003; 4 (2) Article 21 (http://www.pharmscitech.org). 8 pages.

V. Chandrasekhar, "Polymer Solid Electrolytes: Synthesis and Structure", Advances in Polymer Science, 1998, vol. 135, pp. 139-205.

L. Micaroni, et. al., "Considerations About the Electrochemical Estimation of the Ionization Potential of Conducting Polymers", J. Solid State Electrochem., 2002, vol. 7, pp. 55-59.

M. Roemer, et. al., "Microactuators Based on Conducting Polymers", Anal. Bioanal. Chem., 2002, vol. 373, pp. 754-757.

Jörg Müller, et. al., "Development of Facilitated Transport Membranes for the Separation of Olefins from Gas Streams", Desalination, 2002, vol. 145, pp. 339-345.

Petter Danielsson, et. al., "Electrochemical Symthesis and Characterization of Poly(3,4-Ethylenedioxythiophene) in Ionic Liquids with Bulky Organic Anions", J. Solid State Electrochem, 2004, vol. 8, pp. 809-817.

"17. Polymer Electrolytes", 24 pages. Precise date unknown, but before the filing date of the present application.

Ruth Duncan, "The Dawning Era of Polymer Therapeutics", Nature Review, Drug Discovery, May 2003 vol. 2, pp. 347-360.

Marek Trojanowicz, "Application of Conducting Polymers in Chemical Analysis", Microchimica Acta, 2003, vol. 143, pp. 75-91.

Xi Zhang, et. al., "Layered Nanoarchitectures Based on Electro- and Photo-Active Building Blocks", in Multilayer Thin Films, edited by Gero Decher, et. al., Wiley, 2002, pp. 301-330.

M. J. Vicent, et. al., "Polymer Therapeutics: New Platform for Combination Therapy in the Treatment of Hormone-Dependent Cancers", 1 page. Precisse date unknown, but prior to the filing date of the present application.

Jennifer L. Young, et. al., "Nonviral Gene Transfer Strategies for the Vasculature", 2002, Microcirculation, vol. 9, pp. 35-50.

Saulius Šatkauskas, et. al., "Electroporation as a Tool for Biotechnology and Medicine with Specific Emphasize On Its Application for Drug and Gene Delivery. Review", Veterinarija IR Zootechnika. T., 26 (48) 2004, pp. 74-81.

Shaoqin Liu, et. al., "Functional Polyoxometalate Thin Films Via Electrostatic Layer-by-Layer Self Assembly", Journal of Cluster Science, vol. 14, No. 3, Sep. 2003, pp. 405-418.

Xiaoming Yang, et. al., "Imaging of Vascular Gene Therapy", Radiology, 2003 vol. 228, pp. 36-49.

Nagendu B. Dev, et. al., "Sustained Local Delivery of Heparin to the Rabbit Arterial Wall With an Electroporation Catheter", Catheterization and Cardiovascular Diagnosis, 1998, vol. 45, pp. 337-345.

David A. Dean, "Electroporation of the Vasculature and the Lung", DNA and Cell Biology, 2003, vol. 22, No. 12, pp. 797-806.

Wang, et. al. "New Polyoxometalate/Starch Nanomaterial: Synthesis, Characterization and Antitumoral Activity", Dalton Trans., 2003, pp. 957-960.

J. Gehl, "Electroporation: Theory and Methods, Perspectives for Drug Delivery, Gene Therapy and Research", Acta Physiol. Scand., 2003, vol. 177, pp. 437-447.

Ronit Satchi-Fainaro, et. al., "Drug Delivery Systems to Target the Tumour Vasculature and the Tumour Cell", Technology/Industry Overviews, pp. 43-49. Precise date unknown, but prior to the filing date of the present application.

A. R. Kucernak, et. al., "Analysis of the Electrical and Mechanical Time Response of Solid Polymer-Platinum Composite Membranes", Electrochimica Acta, 2000, vol. 46, pp. 1313-1322.

Bruno Scheller, et. al., "Paclitaxel Balloon Coating, a Novel Method for Prevention and Therapy of Restenosis", Circulation, Aug. 17, 2004, pp. 810-814.

Bhavana Deore, et. al. "Overoxidized Polypyrrole with Dopant Complementary Cavities as a New Molecularly Imprinted Polymer Matrix", Analytical Sciences, Sep. 1999, vol. 15, pp. 827-828.

Zhidong Chen, et. al. "Enantioselective Uptake of Amino Acid with Overoxidized Polypyrrole Colloid Templated with L-Lactate", The Analyst, 2000, vol. 125, pp. 2249-2254.

Hiroshi Shiigi, et. al., "Molecularly Imprinted Overoxidized Polypyrrole Colloids: Promising Materials for Molecular Recognition", Microchimica Acta, 200, vol. 143, p. 155-162.

Anne-Valérie G. Ruzette, et. al., "Melt-Formable Block Copolymer Electrolytes for Lithium Rechargeable Batteries", Journal of the Electrochemical Society, 2001, vol. 148, No. 6, pp. A537-A543.

Xuezheng Wang, et. al., "Visualizing Ion Currents in Conjugated Polymers", pp. 1-15. Precise date unknown, but prior to the filing date of the present application.

Rosemary R. Palmer, et. al., "Biological Evaluation and Drug Delivery Application of Cationically Modified Phospholipid Polymers", Biomaterials, 2004, vol. 25, pp. 4785-4796.

K. Jüttner, et. al., "Electrochemical Measurements of the Ion Conductivity, Permselectivity and Transference Numbers of Polypyrrole and Polypyrrole Deriviatives", J. Solid State Electrochem., 1998, vol. 2, pp. 60-66.

György Inzelt, et. al., "Electrochemical Quartz Crystal Microbalance Study of Ion Transport Accompanying Charging-Discharging of Poly(pyrrole) Films", J. Solid State Electrochem., 1999, vol. 3, pp. 251-257.

Mary Ann B. Meador, et. al., PowerPoint presentation, "Evaluation of Rod-Coil Polyimides as Membrane Materials for Lithium Polymer Batteries", NASA Glenn Research Center, 16 pages. Precise date unknown, but prior to the filing date of the present application.

Sreenath Subrahmanyam, PhD Thesis, "Design of Molecularly Imprinted Polymers for Sensors and Solid Phase Extraction", Apr. 2002, Cranfield University Institute of BioScience and Technology, 141 pages.

Hiroshi Shiigi, et. al., "Highly Selective Molecularly Imprinted Overoxidized Polypyrrole Colloids: One-Step Preparation Technique", Analytical Sciences, Jan. 2002, vol. 18, pp. 41-44.

E. W. Damen, et. al., "Paclitaxel Esters of Malic Acid as Prodrugs with Improved Water Solubility", Bioorg Med Chem., Feb. 2000, vol. 8, No. 2, pp. 427-432. Abstract.

Zhiping Deng, et. al., "Characterization of Polymer Films of Pyrrole Derivatives for Chemical Sensing by Cyclic Voltammetry, X-Ray Photoelectron Spectroscopy and Vapour Sorption Studies", *Analyst*, Oct. 1997, vol. 122, pp. 1129-1138.

A. Glidle, et. al., "XPS Assaying of Electrodeposited Copolymer Composition to Optimise Sensor Materials", *Journal of Electron Spectroscopy and Related Phenomena*, 2001, vol. 121, pp. 131-148.

Atsushi Morisato, et. al., "Transport Properties of PA 12-PTMO/ $AgBF_4$ Solid Polymer Electrolyte Membranes for Olefin/Paraffin Separation", *Desalination*, 2002, vol. 145, pp. 347-351.

Dezhi Zhou, et. al., "Solid State Actuators Based on Polypyrrole and Polymer-in-ionic Liquid Electrolytes", *Electrochimica Acta*, 2003, vol. 48, pp. 2355-2359.

Hiroyuki Ohno, et. al., "Development of New Class of Ion Conductive Polymers Based on Ionic Liquids", *Electrochimica Acta*, 2004, vol. 50, pp. 225-261.

* cited by examiner

INTERNAL MEDICAL DEVICES FOR DELIVERY OF THERAPEUTIC AGENT IN CONJUNCTION WITH A SOURCE OF ELECTRICAL POWER

BACKGROUND OF THE INVENTION

Medical devices are known which deliver drugs by iontophoresis, a process by which an electric field is used as a driving force to move a drug into a subject. This technique typically requires two or more electrodes for creating an electric field as well as a drug that carries a net electrical charge at the local physiological pH.

Medical devices are also known which rely on electroporation to enhance drug delivery to cells. The electroporation method uses short, high-voltage pulses to create transient pores in the cell membranes or in organelles within the cells. This transient, permeabilized state can be used to load cells and organelles with a wide variety of therapeutic agents, for example, genes, proteins, small molecule drugs, dyes, tracers, and so forth. Electroporation has already proven to be effective in both chemotherapy and gene therapy, including vascular gene therapy and endovascular treatment. See, e.g., Dean, "Electroporation of the Vasculature and the Lung," *DNA and Cell Biology*, 22 (12), 2003, p. 797; Yang, "Imaging of Vascular Gene Therapy," *Radiology* 2003; 228:36-49; Duncan, "The Dawning Era of Polymer Therapeutics," *Nature Reviews, Volume* 2, May 2003, p. 347; Lavasanifar et al., *Advances Drug Delivery Reviews*, 54 (2002) 169, each of which is incorporated by reference in its entirety.

Unfortunately, the effective in vivo electroporation of vascular tissues is commonly hindered by anatomy, which restricts electrode placement and thus options for optimized electric field distribution.

For example, referring now to FIG. 1A, it is known to provide first and second electrodes E1 and E2 within a porous balloon 110 of a catheter 100. The catheter 100 is inserted into a body lumen such as the lumen formed by a blood vessel wall 150, for example, over a previously inserted guide wire E1, and placed at the desired location within the lumen. The porous balloon 110 is inflated so that blood flow is transiently obstructed, and a drug solution is infused into the balloon. Because of the porous nature of the balloon, the drug can be delivered to the vessel wall. The electrode system uses the guide wire E1 as one electrode and an internal wrapped wire E2 contained within the balloon 110 as the second electrode. When a voltage is applied between the two electrodes, an electric field develops, causing electroporation of the surrounding vessel wall 150 and delivery of drug to cells within the vessel wall.

Unfortunately, such an electrode configuration, in which both electrodes are positioned within the vessel lumen, does not provide an electric field in which a vector of the field (e.g., a primary or secondary field vector) is pointed toward the vessel wall.

Other electrode configurations have been developed to address this issue. For example, referring now to FIG. 1B, it is also known to deliver a molecule such as DNA by electroporation to a vessel wall 150 using a catheter 100 having electrodes E1 and E2 (e.g., two stainless steel electrodes) positioned outside of the vessel wall 150, on opposite sides of the vessel wall 150 (i.e., the field is applied from the electrodes at the adventitial surface of the vessel 150). In use, the catheter 100 is positioned in the vessel 150, balloons 115a, 115b are inflated, and DNA is released into the volume between the balloons 115a, 115b. Once the lumen is filled with DNA, square-wave electric pulses are delivered to the electrodes E1, E2. Unlike the electrode configuration of FIG. 1A, by placing the electrodes on opposite sides of the adventitial surface of the vessel 150, an electric field is provided in which a vector of the field is pointed in the direction of the vessel wall. However, such a procedure is more complicated than that associated with FIG. 1A, as the two electrodes must be positioned outside of the vessel 150. The construction as described in FIG. 1B also has the disadvantage that the drug is provided within a solution and is able to freely flow in any direction. Non-homogeneity of the electric field will therefore cause a non-homogeneous distribution of the drug. Using paclitaxel as a specific example, it is known that the dose for this drug has to be within a relatively narrow window to be effective, which is made difficult by a system that uses a fluid carrier.

Another disadvantage of currently used electroporation delivery systems such as those above is the need for an additional lumen and ports to accommodate a pressurized drug infusion.

Drug delivery in conjunction with a balloon coated with a drug loaded hydrogel has also been attempted. However, up to 65% of the drug was washed from the balloon within 60 secs of exposure to flowing blood. Noel Caplice and Robert Simari, "Gene Transfer for Coronary Restenosis," Novel Revascularization Strategies, Current Interventional Cardiology Reports 1999, 1: pp. 157-164, which is incorporated by reference in its entirety.

The above and other drawbacks of prior devices are addressed by various aspects of the present invention, in which various improved devices are provided for delivery of therapeutic agents based on electric field effects (i.e., delivery is electrically assisted), such as iontophoresis, electroporation, or both.

SUMMARY OF THE INVENTION

The invention generally relates to internal (e.g., implantable, insertable, etc.) drug delivery devices which contain the following: (a) one or more sources of one or more therapeutic agents; (b) one or more first electrodes, (c) one or more second electrodes and (d) one or more power sources for applying voltages across the first and second electrodes. The power sources may be adapted, for example, to promote electrically assisted therapeutic agent delivery within a subject, including electroporation and/or iontophoresis.

In one aspect of the invention, the first and second electrodes are adapted to have tissue of a subject positioned between them upon deployment of the medical device within the subject, such that an electric field may be generated, which is directed into the tissue. Furthermore, the therapeutic agent sources are adapted to introduce the therapeutic agents into the electric field.

In another aspect of the invention, the therapeutic agent sources are polymeric regions that contain one or more types of ion-conductive polymers and one or more types of charged therapeutic agents.

In yet another aspect of the invention, the therapeutic agent sources are polymeric regions that contain one or more types of electrically conductive polymers and one or more types of charged therapeutic agents.

An advantage of the present invention is that internal medical devices may be provided in which electrically assisted therapeutic agent delivery is enhanced, because a vector of the electric field is directed into surrounding tissue.

Another advantage of the present invention is that internal medical devices may be provided, in which electrically assisted therapeutic agent delivery is achieved, without the need for lumens and ports to accommodate pressurized drug infusion.

These and other aspects, embodiments and advantages of the present invention will become readily apparent to those of ordinary skill in the art upon review of the Detailed Description and Claims to follow.

DETAILED DESCRIPTION

Figure 1A:
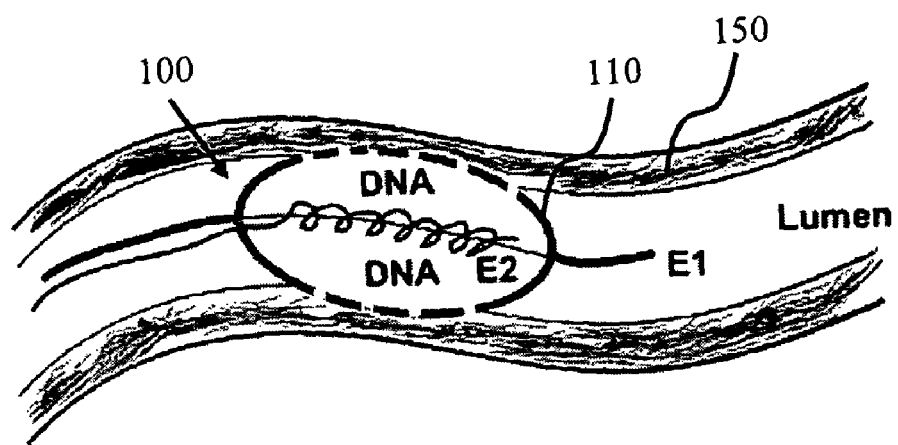
FIG. 1A is a schematic partial cross-sectional view, illustrating a method of delivering a therapeutic agent to body lumen wall via electroporation, in accordance with the prior art.

A more complete understanding of the present invention is available by reference to the following detailed description of various aspects and embodiments of the invention. The detailed description of the invention which follows is intended to illustrate but not limit the invention. The scope of the invention is defined by the claims.

As noted above, the invention generally relates to internal (e.g., implantable, insertable, etc.) drug delivery devices which contain the following: (a) one or more sources of one or more therapeutic agents; (b) one or more first electrodes, (c) one or more second electrodes and (d) one or more power source for applying voltages across the first and second electrodes. The power sources may be adapted, for example, to promote electrically assisted therapeutic agent delivery within a subject, including electroporation and/or iontophoresis.

For example, according to one aspect of the invention, the therapeutic agent sources are polymeric regions that contain one or more types of electrically conductive polymers and one or more types of charged therapeutic agents.

In another aspect, the therapeutic agent sources are polymeric regions that contain one or more types of ion-conductive polymers and one or more types of charged therapeutic agents.

The use of such a polymeric region is advantageous, for example, in that when placed between the first and second electrodes, they allow for close electrode spacing (e.g., by preventing electrode shorting), which in turn leads to increased electric fields for driving charged therapeutic agents. Moreover, in the absence of an electrical field, the mobility of the therapeutic agent is sufficiently low to prevent excessive washout of the therapeutic agent while the device is being positioned, or the direction of the electric field can be manipulated to retain the therapeutic agent within the device. Furthermore, in contrast to devices like that of FIG. 1B above, where the therapeutic agent is provided within a solution and is able to freely flow in any direction, by placing the therapeutic agent within a polymer region, movement of the therapeutic agent is restricted and thus more precise local dosing of the therapeutic agent is possible. This design is also advantageous in that it allows one to provide different therapeutic agents or different therapeutic agent dosages for different sections of the device, which can be beneficial in various instances (e.g., where vulnerable plaque is located on one side of a vessel). In addition, medical devices can be constructed for therapeutic agent delivery, which may avoid the need for complicated designs with separate pressurized drug infusion lumens and ports.

According to another aspect of the invention, the first and second electrodes are adapted to have tissue (i.e., a collection of living or non-living cells, which are associated with a wide range of bodily structures, including (a) muscle tissue, such as skeletal muscle, cardiac muscle and smooth muscle, (b) epithelial tissue lining surfaces on the interior of the body, otherwise known as endothelium), (c) nervous tissue, and (d) connective tissue, such as ligaments, tendons, cartilage, bone, adipose tissue and fibrous tissue, including that found in atherosclerotic plaque, but not including fluid tissue such as blood and lymph) of a subject positioned between them upon deployment of the medical device within the subject, such that an electric field may be generated, which has a vector that is directed into the tissue. Furthermore, the therapeutic agent sources are adapted to introduce the one or more therapeutic agents into the as-generated electric field. This may result, for example, in increased electroporation efficiency, increased iontophoresis efficiency (e.g., where one or more charged therapeutic agents are employed), or both. As used herein "deployment" may consist of simply implanting or inserting a device into a patient, or it may involve further steps beyond implantation or insertion, such as steps in which the device is expanded within the subject.

In certain embodiments of this additional aspect of the invention, the therapeutic agent sources are polymeric regions containing one or more polymers and one or more therapeutic agents.

In certain other embodiments, the one or more therapeutic agents are charged therapeutic agents.

In certain further embodiments, the one or more first electrodes are adapted to penetrate tissue surrounding the medical device.

Internal medical devices benefiting from the various aspects and embodiments of the present invention are numerous and may be selected, for example, from the following: catheters (e.g., renal or vascular catheters such as balloon catheters), balloons, guide wires, filters (e.g., vena cava filters), stents (including coronary vascular stents, peripheral vascular stents, cerebral, urethral, ureteral, biliary, tracheal, gastrointestinal and esophageal stents), stent grafts, vascular grafts, vascular access ports, embolization devices including cerebral aneurysm filler coils (such as Guglilmi detachable coils and various other metal coils), myocardial plugs, septal defect closure devices, patches, pacemakers and pacemaker leads, defibrillation leads and coils, left ventricular assist hearts and pumps, total artificial hearts, heart valves, vascular valves, tissue engineering scaffolds for in vivo tissue regeneration, biopsy devices, as well as many other devices that are implanted or inserted into the body and from which therapeutic agent is released.

The medical devices of the present invention include internal medical devices that are used for diagnosis, for systemic treatment, or for the localized treatment of any tissue or organ, for example, the following: tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, and cartilage. As used herein, "treatment" refers to the prevention of a disease or condition, the reduction or elimination of signs or symptoms associated with a disease or condition, or the substantial or complete elimination of a disease or condition. Typical subjects (also referred to as "patients") are vertebrate subjects, more typically mammalian subjects, and even more typically human subjects.

Hence, in certain embodiments, devices in accordance with the present invention are adapted for delivery of therapeutic agents into tissue. For example, the devices can be used to deliver therapeutic agents into various tissue surfaces, including the exterior walls of tissue such as the wall of the heart and the bladder, among others. Therapeutic agent can also be delivered to lumen walls, for example, those corresponding to the following: lumens of the cardiovascular system such as the heart, arteries (e.g., coronary, femoral, aorta, ilial, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract, such as the trachea, bronchi, nasal passages and sinuses, lumens of the gastrointestinal tract such as the esophagus, gut, duodenum, small intestine, large intestine, colon, biliary and pancreatic duct systems, lumens of the lymphatic system, the major body cavities (peritoneal, pleural, pericardial), and so forth.

As noted above, various aspects of the invention utilize polymeric regions containing one or more polymers and one or more therapeutic agents.

By a "polymeric" region is meant a region that contains polymers, commonly at least 50 wt %, 75 wt %, 90 wt %, 95 wt % or even more, polymers.

As used herein, "polymers" are molecules that contain containing multiple copies of the same or differing constitutional units, commonly referred to as monomers, and typically containing from 5 to 10 to 25 to 50 to 100 or more constitutional units. Depending on the number and nature of the polymer chains making them up, the polymers for use in the present invention may have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others. The polymers may contain, for example, homopolymer chains, which contain multiple copies of a single constitutional unit, and/or copolymer chains, which contain multiple copies of at least two dissimilar constitutional units, which units may be present in any of a variety of distributions including random, statistical, gradient, and periodic (e.g., alternating) distributions. "Block copolymers" are polymers containing two or more differing polymer chains, for example, selected from homopolymer chains and random and periodic copolymer chains.

Ion-conductive polymeric regions are polymeric regions that permit movement of ions, and in the present invention, permit movement of charged therapeutic agents. Like other ionic species, charged therapeutic agents move in response to concentration gradients (via a process called "diffusion") and in response to electric fields (via a process called "migration"). In order to enhance mobility, ion-conductive polymeric regions may contain one or more amorphous, low glass transition temperature ($T_g$) polymer chains. Whether or not a polymer chain is amorphous can be determined by observing the thermal transitioning of the polymer matrix using a differential scanning calorimeter (DSC). As used herein, "low $T_g$ polymer chains" are those that display a $T_g$ that is below ambient temperature, more typically below about 20° C., below about 0° C., below about −25° C., or even below about −50° C. Conversely, elevated or "high $T_g$ polymer chains" are those that display a glass transition temperature that is above ambient temperature, more typically above 50° C., above 75° C., or even above 100° C. or more. $T_g$ can be measured by any of a number of techniques including differential scanning calorimetry (DSC), dynamic mechanical analysis (DMA), or dielectric analysis (DEA). "Ambient temperature" is typically 25° C.-45° C., more typically body temperature (e.g., 35° C.-40° C.). Mobility within ion-conductive polymeric regions is also known to be enhanced by the use of plasticizers such as ethylene carbonate, propylene carbonate, diethyl phthalate, and other plasticizers.

In addition to allowing ion movement, ion-conductive polymeric regions are also capable of maintaining therapeutic agents in an ionized form (via a process that is sometimes referred to as "solvation"), as opposed to a charge-neutral form (e.g., in non-ionized acid, base, salt, etc., form). Charge-neutral species are generally not transported in response to an electric field (although they may experience diffusion in response to a concentration gradient). Polymers suitable for maintaining therapeutic agents in ionized form commonly have cation and/or anion coordinating sites, which are capable of forming complexes with ions, or they are themselves ionized.

Suitable ion-conductive homopolymers and copolymers may be selected, for example, from the following: (a) polyethers, such as polyethylene oxide (PEO)(also referred to as polyethylene glycol, particularly at lower molecular weights) and polypropylene oxide (PPO), (b) polysiloxanes such as block copolymers of dimethyl siloxane and ethylene oxide, urethane crosslinked networks of poly(dimethyl siloxane-graft-ethylene oxide), and copolymers based on poly(methyl hydrosiloxane), poly(ethylene glycol) monomethyl ether and poly(ethylene glycol), see, e.g., Liang W-J. et al., "Morphology and Ionic Conductivity Studies of Hybrid Electrolytes based on Epoxide-Crosslinked Polysilane/Polyether Networks," *Macromol. Chem. Phys.* 2004, 205, 600-610, (c) polyphosphazenes such as methoxy ethoxy ethoxy polyphosphazene (MEEP), (d) poly(vinyl pyrrolidines), (e) polyacrylates and polymethacrylates such as poly(methoxy ethoxy ethyl methacrylate) (polyMEEMA) and poly[(ω-carboxy) oligooxyethylene methacrylate], (f) poly(crown ethers), (g) polyelectrolytes, for instance itaconates such as poly[di-ethoxy(3)methyl itaconate] and poly(di-poly(propylene glycol) itaconate), succinates such as poly(ethylene succinate), and adipates such as poly(ethylene adipate), (h) other polymers such as poly(vinyl alcohols), poly(ethylene imines), poly(alkylene sulphides), poly(propiolactones), cellulose acetates, poly(vinyl methyl ketones), poly(hexamethylenevinylenes), poly(styrenes), poly(2-ethyl-2-oxazoline) and blends thereof, among many others.

Optimal homopolymers and copolymers for supporting ionization and transport of charged therapeutic agents within the ion-conducting polymeric regions of the present invention will vary from therapeutic agent to therapeutic agent, with appropriate polymers for a given therapeutic agent being readily determined by those of ordinary skill in the art.

For instance, certain embodiments of the invention employ polymers that form ionized metal-salt complexes. PEO, for example, forms complexes with a range of metal cations including alkali metal cations, alkaline earth metal cations, and transition metal cations. These include a number of mono and divalent cations, such as $Li^+$, $Na^+$, $K^+$, $Cs^+$, $Ag^+$, $Mg^{2+}$, $Ca^{2+}$, $Zn^{2+}$, $Cu^{2+}$ and so forth. Consequently, PEO is capable of stabilizing and transporting such cations, as well as counterions of the same, including various therapeutic agent counterions. In addition, PEO is capable of facilitating transport of uncharged therapeutic agents which are capable of complexing with metal cations. For example, it is known that silver ions simultaneously coordinate with olefins and with polymers, allowing the facilitated transport of olefins in a variety of polymers including, for example, PEO as well as cellulose acetate, poly(vinyl methyl ketone), poly(hexamethylenevinylene), poly(styrene), poly(N-vinyl pyrrolidone), and poly (2-ethyl-2-oxazoline), among others.

Certain other embodiments of the invention employ polyelectrolytes as ion-conductive polymers. Polyelectrolytes are polymers having multiple (e.g., 5, 10, 25, 50, 100, or more) charged sites (e.g., ionically dissociable groups). Thus, as defined herein, the term polyelectrolyte embraces a wide range of species, including polycations and their precursors (e.g., polybases), polyanions and their precursors (e.g., polyacids), polymers having multiple anionic and cationic groups (e.g., polymers having multiple acidic and basic groups), ionomers (polyelectrolytes in which a small but significant proportion of the constitutional units carry charges), and so forth.

For example, polymeric regions in accordance with the present invention may contain an essentially immobile polyelectrolyte polycation or polyanion, as well as a mobile therapeutic agent of opposite charge.

Depending on the type of dissociable groups, many polyelectrolytes are classified as polyacids and polybases. When dissociated, polyacids form polyanions, with protons being split off. Polybases, on the other hand, contain groups which are capable of accepting protons, thereby forming polycations. Polyelectrolyte molecules may be crosslinked to increase stability.

In addition to itaconate, succinate and adipate polyanions such as those listed above, further specific examples of polyanions include poly(styrenesulfonate) polyanions (e.g., poly (sodium styrene sulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions, among many others. Specific examples of polycations include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations, among many others.

Certain other embodiments of the present invention employ ion-transporting polymeric regions which are based on ionic liquids. For example, ion-transporting polymers have been formed by polymerization of monomers derived from ionic liquids, including (a) monomers based on an imidazolium (i.e., ethyl imidazolium) cation and a mono/polyether spacer, such as

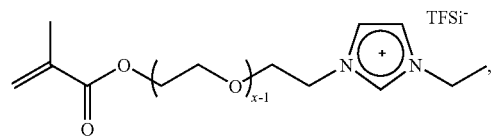

where TFSI represents bis(trifluoromethanesulfonyl)imide, where x is an integer, for example ranging from 2-10, (b) monomers based on an imidazolium cation and an alkyl spacer such as

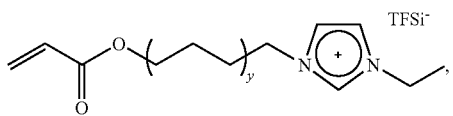

where y is a multiple of 0.5 (e.g., 1, 1.5, 2, 2.5, etc.), for example ranging from 1 to 10, (c) monomers based on a sulfonate anion, and an alkyl spacer, such as

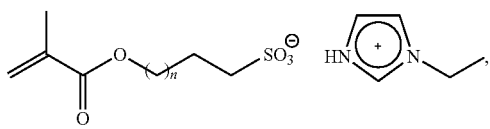

where n is an integer, for example, ranging from 1 to 20, and (d) monomers based on the sulfonate anion and a mono/polyether spacer, such as

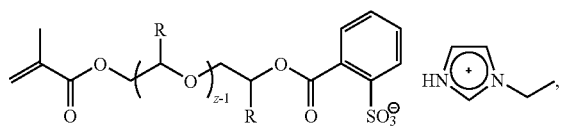

where n is an integer, for example, ranging from 1 to 10, and R is hydrogen or alkyl (e.g., methyl, ethyl, etc.). Further details can be found, for example, in H. Ohno et al., "Development of new class of ion conductive polymers based on ionic liquids," *Electrochimica Acta* 50 (2004) 255-261, which is incorporated by reference in its entirety. Such polymers are technically polycations and polyanions.

Ion-conductive polymeric regions have also been prepared from ionic liquid electrolytes by polymerizing a monomer (e.g., methyl methacrylate) in the presence of the ionic liquid electrolytes (e.g., 1-ethyl-3-methylimidazolium bis(trifluoromethylsulfonyl) amide and/or 1-butyl-3-methylimidazolium), thereby forming a solid matrix for the ionic liquid electrolytes. Electrolytes of this type have been shown to function effectively in conjunction with polypyrrole solid state actuators. D. Zhou et al., "Solid state actuators based on polypyrrole and polymer-in-ionic liquid electrolytes," *Electrochimica Acta* 48 (2003) 2355-2359 which is incorporated by reference in its entirety.

Certain further embodiments of the invention employ conductive polymers. Conductive polymers commonly feature a conjugated backbone (e.g., they have a backbone that contains an alternating series of single and double carbon-carbon bonds). Some commonly known conductive polymers are polypyrroles, polyanilines, polythiophenes, polyethylenedioxythiophenes, poly(p-phenylene vinylene)s, polysulfones and polyacetylenes. Polypyrrole, which is one of the more stable of these polymers under physiological conditions, is pictured below:

Known derivatives of polypyrrole include the following substituted polymers: poly(N-methylpyrrole), poly(N-butylpyrrole), poly[N-(2-cyanoethyl)pyrrole], poly[N-(2-carboxyethyl)pyrrole], poly(N-phenylpyrrole), poly[N(6-hydroxyhexyl)pyrrole], and poly[N-(6-tetrahydropyranylhexyl)pyrrole], among others.

Conductive copolymers may also be formed from the above and other monomers (e.g., from pyrrole monomers, aniline monomers, thiophene monomers, ethylenedioxythiophene monomers, p-phenylene vinylene monomers, sulfone monomers, acetylene monomers, etc). For instance, pyrrole copolymers can be formed, for example, from two or more of the following monomers: pyrrole, 1-(2-cyanoethyl) pyrrole, 1-phenylpyrrole, 3-(acetic acid)pyrrole, 1-(propionic acid)pyrrole, and the pentafluorophenol ester of the same, among others. Specific examples include, for example poly[pyrrole-co-3-(acetic acid)pyrrole], poly[pyrrole-co-1-(propionic acid)pyrrole], poly[pyrrole-co-1-(propionic acid) pyrrole pentafluorophenol ester], poly[pyrrole-co-1-(2-cyanoethyl)pyrrole] and poly(pyrrole-co-1-phenylpyrrole), among others. For further information, see, e.g., Glidle A. et al., "XPS assaying of electrodeposited copolymer composition to optimise sensor materials," *Journal of Electron Spectroscopy and Related Phenomena*, 121 (2001) 131-148, which is incorporated by reference in its entirety.

Electrically conductive polymers are typically semi-conductors in their neutral state. However, upon oxidation or reduction of the polymer to a charged state (e.g., polypyrrole is positively charged when oxidized and is neutral when reduced), the electrical conductivity is understood to be changed from a semi-conductive regime to a semi-metallic regime. Oxidation and reduction are believed to lead to charge imbalances that, in turn, can result in a flow of ions into or out of the material. These ions typically enter/exit the material from/into an ionically conductive medium associated with the polymer. For example, it is well known that dimensional changes are effectuated in electroactive polymers (EAPs), including conductive polymers, by the mass transfer of the ions (which are surrounded by a shell of water molecules, commonly referred to as the "hydration shell") into or out of the polymers. For example, in some conductive polymers, expansion is believed to be due to ion insertion between chains, whereas in others, inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 30%). As used herein, the expansion or the contraction of the conductive polymer is generally referred to as "actuation."

When in a charged state, conductive polymers resemble polyelectrolytes, with certain characteristics similar to the above-described polyelectrolytes. However, unlike the polyelectrolytes above, these polymers are not considered to be ion-conductive polymers for the purposes of the present invention. For example, they are electrically conductive,

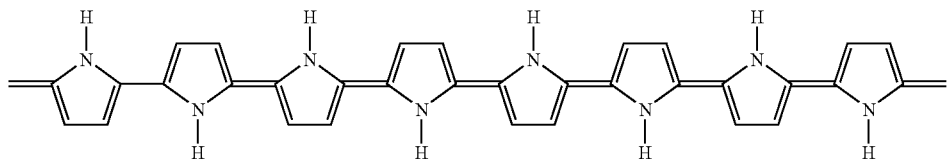

making it difficult to establish significant electrical potential gradients (electric fields) within them, which is required for ion migration.

Nonetheless, the fact that oxidation and reduction of conductive polymers is associated with the flow of ions into or out of the material, makes these materials useful for retention and/or delivery of charged therapeutic agents. Indeed, it has been reported in a study by Michel et al. that superior thrombolysis is achieved with combined mechanical and pharmacologic therapy, for example, via local delivery using a hydrogel balloon. See, e.g., Michel et al., "Catheter-Based Local Thrombolysis With Urokinase: Comparative Efficacy of Intraluminal Clot Lysis With Conventional Urokinase Infusion Techniques in an In Vivo Porcine Thrombus Model," *Catheterization and Cardiovascular Diagnosis* 41: 293-302 (1997). Hence, the actuating properties of polypyrroles and other conductive polymers allows them to provide a mechanical component to the therapy, making them particularly desirable for delivery of charged therapeutic agents in accordance with the present invention, for example, in conjunction with electroporation procedures.

Redox switching of conductive polymers may allow a number of different oxidation states to be accessible. These redox states are stabilized by charge-balancing counter ions (often called dopant ions), which move in and out of the polymer during electrochemical switching. As a specific example, a variety of charge-balancing anions, including negatively charged therapeutic agents, may be associated with an oxidized, positively charged, conductive polymer, such as polypyrrole. However, by reducing/neutralizing the polymer, a net negative charge develops within the polymer, resulting in expulsion of the anions from the polymer. Further information regarding the use of conductive polymers for ion delivery can be found, for example, U.S. Patent Appln. Pub. No. 2002/0022826 which is incorporated by reference in its entirety. See also H. Huang et al., "Probe beam deflection study on electrochemically controlled release of 5-Fuorouracil," *Electrochimica Acta*, Vol. 43, No. 9, pp. 999-1004, 1998; S.-K. Lee et al., "Experimental Analysis on the Properties of Polypyrrole as Drug Delivery System Materials," *Smart Structures and Materials* 2003: *Electroactive Polymer Actuators and Devices* (EAPAD), Yoseph Bar-Cohen, Editor, Proceedings of SPIE Vol. 5051 (2003) which describes the delivery of charged drugs such as salicylate and epinephrine from polypyrrole; R. L. Blankspoor and L. L. Miller, "Polymerized 3-Methoxythiophene. A Processable Material for the Controlled Release of Anions," *J. Chem. Soc., Chem. Commun.*, pp. 90-92 (1985) which describes the delivery of glutamate ions from 3-methoxythiophene; A.-C. Chang and L. L. Miller, "Electrochemically Controlled Binding and Release of Salicylate, TCNQ'- and Ferrocyanide from Films of Oligomeric 3-Methoxythiophene," J. Electroanal. Chem., 247 (1988) 173-184; B. Zinger and L. L. Miller, "Timed Release of Chemicals from Polypyrrole Films," *J. Am. Chem. Soc.* 1984, 106, 6861-6863, which describes the release of glutamate ions from polypyrrole; B. Pirot et al., "Electrochemical method for entrapment of oligonucleotides in polymer-coated electrodes," J. Biomed. Mater. Res., 1999, 46(4), 566-72, which describes the incorporation of oligonucleotides into conducting films of poly(3,4-ethylene dioxythiophene)—the addition of neutral water soluble polymers such as poly(vinylpyrrolidone) or poly(ethylene glycol) resulted in higher incorporation yields of oligonucleotides. Each of these is incorporated by reference in its entirety.

In certain embodiments of the present invention, overoxidized conductive polymers are used for delivery of charged therapeutic agents from internal medical devices, for example, in conjunction with electroporation.

Overoxidized pyrrole has been used for molecular recognition. Specifically, it is known that overoxidation of polypyrrole films can create a cavity complementary to the molecular shape of a dopant anion (e.g., an amino acid such as L-glutamic acid) and that such films can be utilized as polymer receptors. Polymer colloids (e.g., of polyaniline and polypyrrole colloids) can also be overoxidized to produce polymer receptors. Overoxidized polymer colloids have demonstrated high enantioselectivity towards various amino acids. The selectivity may be explained in terms of the cavity that is created by the dedoping process (extraction of a dopant) occurring concomitantly with irreversible overoxidation of the polymer. Colloids dispersed in aqueous organic and inorganic electrolytes can take up and eject their anions by controlling the potential in solution. For more information see, e.g., B. Deore et al., "Overoxidized Polypyrrole with Dopant Complementary Cavities as a New Molecularly Imprinted Polymer Matrix," *Anal. Sci.* Vol. 15, 1999, 827-829; Z. Chen et al., "Enantioselective uptake of amino acid with overoxidized polypyrrole colloid templated with L-lactate," Analyst, 2000, 125, 2249-2254; H. Shiigi et al., "Molecularly Imprinted Overoxidized Polypyrrole Materials for Molecular Recognition," Microchim. Acta 143, 155-162 (2003), each of which is incorporated by reference in its entirety.

Polymeric regions for use in various embodiments of the invention may also be provided with components in addition to species such as conductive polymers, ion-conductive polymers, ionic liquids, etc. (which give them ion-conductive and/or electrically conductive characteristics), including polymeric or inorganic components, which modify these or other characteristics of the polymeric region.

For example, in some embodiments, a non-ion-conductive, non-conductive polymer is used to provide desired mechanical or other characteristics. Suitable polymers can be selected, for example, from various homopolymers and copolymers listed in paragraph [54] of U.S. Patent Application Pub. No. 2003/0236514, which is incorporated by reference in its entirety. Combinations (e.g., blends) often combine desirable characteristics of each polymer. As a specific example, polyaniline, which is electrically conductive but is brittle and lacks thermal stability, has been blended with polyimide to address these drawbacks. See, e.g., M. G. Han et al., "X-ray photoelectron spectroscopy study of electrically conducting polyaniline/polyimide blends," *Polymer* 41 (2000) 3253-3262, which is incorporated by reference in its entirety.

As another specific example, in some embodiments, block copolymers are utilized, which contain (a) ion-conductive and/or electrically conductive polymer chains such as those described above and (b) homopolymer and/or copolymer chains (selected, for example, from chains based on the various homopolymers and copolymers listed in paragraph [54] of U.S. Patent Application Pub. No. 2003/0236514).

Inorganic materials may also be provided within the polymeric regions of the invention. For instance, such polymeric regions may contain (a) one or more polymeric phases that contain conductive polymers, ion-conductive polymers, ionic liquids, etc. and (b) one or more inorganic phases that contain inorganic materials. In some cases, the polymeric and inorganic phases may interact with one another by relatively weak forces (e.g., Van der Waals forces, ionic forces, hydrogen bonding, and so forth). In other cases, these phases are linked together through stronger forces (e.g., covalent bonds, coordination bonding, and ionic-coordination bonding).

Examples of inorganic materials include metallic materials and non-metallic materials, such as carbon-based materials, silicon-based materials, germanium-based materials and metal oxides. Specific examples include silicon and germanium oxides, and metal oxides (e.g., transition metal oxides, tin oxide, etc.), including polyoxometalates, and crystalline compounds such as crystalline antimonic acid, among many others See, e.g., Gomez-Romero, P. et al., "Hybrid Organic-Inorganic Materials—In Search of Synergic Activity," *Adv. Mater.* 2001, 13, No. 3, Feb. 5; Zhonghua Peng, "Rational Synthesis of Covalently Bonded Organic-Inorganic Hybrids," *Angew. Chem. Ind. Ed.*, 2004, 43, 930-935; Beleze, F. A. et al., "Synthesis and Characterization of Organic-Inorganic Hybrids Formed between Conducting Polymers and Crystalline Antimonic Acid," *J. Braz. Chem., Vol.* 12, No. 4, 542-547, 2001; MacLachian M. J. et al., "New (inter)Faces: Polymers and Inorganic Materials," *Adv. Mater.*, 2000, 12, No. 9, pp. 675 et seq, each of which is incorporated by reference in its entirety.

In certain aspects and embodiments of the invention (e.g., certain electroporation embodiments), non-charged therapeutic agents may be employed, which may be released from a variety of sources, including polymeric regions which may, or may not, be capable of ion transport or electrical conductivity (e.g., they may, or may not, contain ion-conductive or electrically conductive polymers). Suitable homopolymers, copolymers and polymer blends for such polymeric regions may be selected, for example, from those described herein as well as those listed in paragraph [54] of U.S. Patent Application Pub. No. 2003/0236514.

As indicated above, medical devices in accordance with the present invention are therapeutic agent delivery devices. "Therapeutic agents," "drugs," "bioactive agents" "pharmaceuticals," "pharmaceutically active agents", and other related terms may be used interchangeably herein and include genetic and non-genetic therapeutic agents. Therapeutic agents may be used singly or in combination.

A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Therapeutic agents may be selected, for example, from the following: adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, anfifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, anfimigraine agents, antimitotic agents, anfimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immune response modifiers, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine Al antagonists, serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

Some specific beneficial agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well a derivatives of the forgoing, among many others.

In certain aspects and embodiments of the invention, the selected therapeutic agents are charged therapeutic agents. By "charged therapeutic agent" is meant a therapeutic agent that has an associated charge. For example, a therapeutic agent may have an associated charge (a) because it is inherently charged (e.g., because it is an acid, base, or salt), (b) because it has been modified to carry a charge by covalently linking a charged species to it, (c) because it is non-covalently linked to a charged species (e.g., based on hydrogen bonding with the charged species, or because it forms complexes and/or coordinative bonds with charged species), or (d) because it is attached to or encapsulated within a charged particle, such as a charged nanoparticle (i.e., a charged particle of 100 nm or less in diameter), including nanocapsules and charged micelles, among others.

Taking paclitaxel as one specific example, various cationic forms of paclitaxel are known, including paclitaxel methyl pyridinium mesylate and paclitaxel conjugated with N-2-hydroxypropyl methyl amide, which may form complexes with ion-conductive polymers, for instance, an anionic polyelectrolyte such as poly(L-glutamate). Examples of anionic forms of paclitaxel are paclitaxel-poly(1-glutamic acid), paclitaxel-poly(1-glutamic acid)-PEO. In addition to these, U.S. Pat. No. 6,730,699, which is incorporated by reference in its entirety, also describes paclitaxel conjugated to various other polymers including poly(d-glutamic acid), poly(dl-glutamic acid), poly(1-aspartic acid), poly(d-aspartic acid), poly(dl-aspartic acid), poly(1-lysine), poly(d-lysine), poly(dl-lysine), copolymers of the above listed polyamino acids with polyethylene glycol, polycaprolactone, polyglycolic acid and polylactic acid, as well as poly(2-hydroxyethyl 1-glutamine), chitosan, carboxymethyl dextran, hyaluronic acid, human serum albumin and alginic acid. These can, of course, be associated with various metal cations, including sodium. Still other anionic forms of paclitaxel include carboxylated forms such as 1'-malyl paclitaxel sodium salt (see, e.g. E. W. DAmen et al., "Paclitaxel esters of malic acid as prodrugs with improved water solubility," *Bioorg Med Chem.*, 2000 February, 8(2), pp. 427-32), which is incorporated by reference in its entirety. In this regard, ion-conductive polyethers (e.g., PEO), are known to function well in connection with salts having a mono- or divalent metal cation (e.g., $Li^+$, $Na^+$, $K^+$, $Cs^+$, $Ag^+$, $Mg^{2+}$, $Ca^{2+}$, $Zn^{2+}$, $Cu^{2+}$ etc and a bulky anion.

Polymeric regions for use in the various aspects and embodiments of the present invention may be provided in a variety of forms, including layers that are formed over all or only a portion of an underlying medical device substrate, bulk device regions that do not require an underlying substrate such as scaffolds and fibers, and so forth. Layers can be provided over an underlying substrate at a variety of locations, and in a variety of shapes. They may be stacked on one another. Consequently, one can stack multiple therapeutic agents in multiple layers, which may emerge in series. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Where polymeric regions are formed over all or only a portion of an underlying substrate, the underlying substrate may be formed from a variety of materials including metallic materials and non-metallic materials, such as ceramic materials, carbon-based materials, silicon-based materials, polymeric materials, and so forth.

For example, to enhance coating integrity and stability (e.g., due to improved interaction at the interface between the coating and the substrate), it may be desirable in certain embodiments of the invention to dispose such polymeric regions on substrates that contain the same or related polymer chains, including homopolymer chains and copolymer chains. Homopolymer chains may correspond, for example, to an entire homopolymer or to a chain within a block copolymer. Similarly, copolymer chains may correspond, for example, to an entire non-block copolymer, such as a random or alternating copolymer, or to a chain within a block copolymer. Thus, a homopolymer may be employed within the substrate, the coating, or both; a non-block copolymer may be employed within the substrate, the coating, or both; a block-copolymer may be employed for the substrate, the coating, or both; and so forth.

One example, among many others, is the use of a substrate containing a polymer having a polyamide chain, such as a nylon balloon, which has a polyamide coating such as a poly(amino acid) coating.

Various beneficial substrates and polymeric regions in accordance with the present invention involve the use of block copolymers. As noted above, "block copolymers" are polymers containing two or more differing polymer chains, for example, selected from homopolymer chains and copolymer chains such as random copolymer chains and periodic copolymer chains, among others. Block copolymers are useful in medical devices, for instance, because the chains making up the block copolymers can be varied to tailor the properties of the polymer material.

In certain embodiments, block copolymers for use in the medical devices of the present invention (e.g., as substrates, therapeutic-agent-containing polymeric regions, etc.) contain (a) one or more low $T_g$ polymer chains (designated "L" below) and (b) one or more high $T_g$ polymer chains (designated "H" below).

Block copolymer configurations vary widely and include, for example, the following configurations (in which H and L chains are used for illustrative purposes, although other chains having different characteristics can clearly be substituted): (a) block copolymers having alternating chains of the type $(HL)_m$, $L(HL)_m$ and $H(LH)_m$ where m is a positive whole number of 1 or more, (b) star block copolymers having multi-arm geometries such as $X(LH)_n$, and $X(HL)_n$, where n is a positive whole number of 3 or more, and X is a hub species (e.g., an initiator molecule residue, a residue of a molecule to which preformed polymer chains are attached, etc.), and (c) comb copolymers having a L chain backbone and multiple H side chains and vice versa (i.e., having an H chain backbone and multiple L side chains).

Examples of low $T_g$ polymer chains include polyether chains (i.e., polymer chains containing multiple C—O—C linkages), among many others, whereas examples of high $T_g$ polymer chains include polyamide chains (i.e., polymer chains containing multiple —NH—CO— linkages), among many others. As previously indicated, block copolymers containing polyether chains and polyamide chains can be used in medical devices, for instance, in balloons, catheters and endoscopes, among others. See, for example, U.S. Pat. No. 5,556,383 to Wang et al. for more information. Many polyether-polyamide block copolymers have excellent mechanical properties, are stable, and are readily processed (e.g., by melt or solution processing). Furthermore, as noted above, various polyethers are effective as ion-conductive polymers.

A few specific examples of polyether chains, which may be provided, for example, in homopolymers and copolymers, are those of the formulas, —$[R_1—O—]_n$— or —$[R_1—O—R_2—O]_n$—, where $R_1$ and $R_2$ can be the same or different and may be selected from linear, branched and cyclic alkyl groups, aromatic groups and alkyl-aromatic groups having from 1 to 10 carbon atoms (more typically linear or branched alkyl groups having from 1 to 6 carbons) and where n is an integer of 5 or more, typically 10 or more, 25 or more, 50 or more, 100 or more, 250 or more, 500 or more, or even 1000 or more.

Polyethers may be formed, for example, from ring opening addition polymerization of cyclic ethers, such as ethylene oxide, where $R_1=R_2=$dimethylene (i.e., $-[(CH_2)_2-O]-_n$), which is commonly referred to as polyethylene glycol or as polyethylene oxide), trimethylene oxide, where $R_1=R_2=$trimethylene (i.e., $-[(CH_2)_3-]-_n$), propylene oxide, where $R_1=R_2=$methyl substituted dimethylene (i.e., $-[(CH_2CH_2(CH_3)-O]-_n$, referred to as polypropylene glycol or polypropylene oxide), and tetrahydrofuran, where $R_1=R_2=$tetramethylene (i.e., $-[(CH_2)_4-O]_n$, which is referred to as polytetramethylene glycol, polytetramethylene oxide (PTMO), or terathane).

Examples of polyamide chains, which may be provided, for example, in homopolymers and copolymers, include polyamides of the formula $-[R_3-NH-CO]_m-$ or $-[NH-R_3-NH-CO-R_4-CO]_m-$, where $R_3$ and $R_4$ can be the same or different and may be selected from linear, branched and cyclic alkyl groups, aromatic groups and alkyl-aromatic groups of 1 to 20 carbon atoms (more typically linear or branched alkyl groups having from 1 to 15 carbons, such as methyl, ethyl, propyl, isopropyl, and so forth) and where m is an integer of 5 or more, typically 10 or more, 25 or more, 50 or more, 100 or more, 250 or more, 500 or more, or even 1000 or more. Specific examples include nylons, such as nylon 6, nylon 4/6, nylon 6/6, nylon 6/10, nylon 6/12, nylon 11 and nylon 12 and poly(amino acids) (PAAs) such as poly (L-glutamic acid)

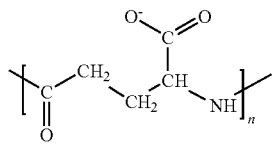

and poly(L-lysine)

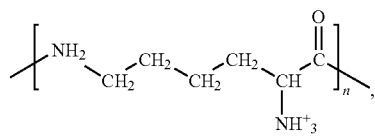

mixed peptides and full length proteins. Note that, due to their net negative and positive charges, poly(L-glutamic acid) and poly(L-lysine), as well as various mixed polypeptides and full length proteins, are polyelectrolytes, which are a class of ion-conductive polymer as noted above. A specific example of a polyether-polyamide block copolymer, which is useful for medical device substrates, therapeutic-agent-containing polymeric regions, and other applications, is poly(tetramethylene oxide)-b-polyamide-12 block copolymer, available from Elf Atochem as PEBAX.

As noted above, polyether-polyamide block copolymers such as PEBAX have excellent mechanical properties, are stable, and are readily processed (e.g., by melt or solution processing). Polyether-polyamide block copolymers such as PEBAX are also capable of forming good interfacial contacts with other materials including metals, ceramics and other polymers, particularly with polyethers, polyamides, and poly (ether-amide) copolymers.

Hence, in certain embodiments of the invention, a medical device substrate containing a polyether-polyamide block copolymer (e.g., a PEBAX balloon) is provided with a polymer coating that contains one or more (i.e., blends) of the following: (a) polyethers including polyether homopolymers and copolymers such as, for example, PEO, PPO, PTMO, and copolymers of two or more of the following: ethylene oxide, propylene oxide, trimethylene oxide and tetramethylene oxide, (b) polyamides including nylon homopolymers and copolymers such as nylon 6, nylon 4/6, nylon 6/6, nylon 6/10, nylon 6/12, nylon 11 and nylon 12, and polyamide polyelectrolytes such as poly amino-acid homopolymers and copolymers such as poly(L-glutamic acid), poly(L-lysine), and mixed poly(amino acids) including peptides and full length proteins, and (c) block copolymers containing one or more polyether chains and one or more polyamide chains, such as those set forth in elements (a) and (b). If desired, these materials may be crosslinked which different agents to achieved desired properties, e.g., to reduce solubility, and so forth.

Polymeric regions containing at least one polymer for use in the present invention may be formed from a variety of techniques, for example, from a solution that contains the following: (a) the at least one polymer and (b) at least one solvent species such as water, acetonitrile, ethanol, THF, methanol, among many others. If desired, various other agents may be added such as (c) at least one therapeutic agent (which may be charged and/or uncharged, depending on the application), and (d) where an uncharged therapeutic agent is provided within a polymeric regions containing an ion-conductive polymer, a charged species may also be included which coordinates/complexes with the therapeutic agent and the polymer to facilitate transport of the therapeutic agent, among many other agents. If the at least one polymer has thermoplastic characteristics, then a melt may be formed, for example, from element (a) and optionally elements (c) and/or (d), among many other agents. Such a solution or melt may then be applied to a substrate (e.g., an underlying medical device substrate or a detachable substrate such as a mold) by a variety of techniques including pouring, dipping, spraying, extrusion, coating with an applicator (e.g., by roller or brush), spin-coating, web coating, techniques involving coating via mechanical suspension including air suspension, ink jet techniques, electrostatic techniques, and combinations of these processes.

Where polyelectrolytes are employed, polymeric coatings may be grown using layer-by-layer techniques. Layer-by-layer techniques can be used to coat a wide variety of substrates via electrostatic self-assembly. In the layer-by-layer technique, a first layer having a first charge is typically deposited on an underlying substrate, followed by a second layer having a second charge that is opposite in sign to the charge of the first layer, and so forth. The charge of the outer layer is reversed upon deposition of each sequential layer. Specific examples include: (a) polyelectrolyte homopolymers and non-block copolymers, for example, poly(amino acid) polyelectrolytes such as poly(L-glutamic acid), poly(L-lysine), poly(mixed amino acid) polyelectrolytes and protein polyelectrolytes, and (b) block copolymers containing one or more polyelectrolyte chains and one or more polyelectrolyte or non-polyelectrolyte chains (e.g., PEO-polyglutamate, PEO-polylysine, etc.). If desired, therapeutic agents may be conjugated to such charged polymers (e.g., paclitaxel-poly (L-glutamic acid), paclitaxel-poly(L-glutamic acid)-PEO, paclitaxel-poly(L-lysine), paclitaxel-poly(L-lysine)-PEO, etc.). Moreover, polyelectrolyte containing species may be cross-linked with other polymers, if desired (e.g., a poly (amino acid) or a paclitaxel-poly(amino acid) conjugate that is crosslinked with PEO, etc.).

Polyelectrolyte-containing species may also be used to form charged particles, such as charged nanoparticles. Such charged particles may in turn participate, for example, in layer-by-layer deposition processes (i.e., one or more of the charged layers may be a layer of charged particles). Moreover, one or more therapeutic agents may optionally be attached to or disposed within such charged particles in order to provide a charged therapeutic agent. In these instances, the charged therapeutic agent (in particulate form) may be delivered from the medical devices of the invention, particularly when the charged, drug-loaded particles are provided at or near the device surface.

Specific examples of charged particles include nanocapsules that contain alternating layers of (a) a polyanion, for example, poly(L-glutamic acid) and (b) a polycation, for example, poly(L-lysine). If desired a charged or uncharged therapeutic agent may be provided within the core of the nanocapsule. For example, see I. L. Radtchenko et al., "A novel method for encapsulation of poorly water-soluble drugs: precipitation in polyelectrolyte multilayer shells," *International Journal of Pharmaceutics*, 242 (2002) 219-223 which is incorporated by reference in its entirety. Therapeutic agent may also be provided within one or more of the layers of the nanocapsule, for instance, by using a charged therapeutic agent (e.g., paclitaxel conjugated to a polycation such as poly-L-lysine or a polyanion such as poly-L-glutamic acid).

Further specific examples of charged particles include charged micelles. For example, poly(ethylene oxide)-block-poly(amino acids) may form charged micelles for drug delivery. In some instances, therapeutic agents have been conjugated to the poly(amino acid) blocks [e.g., poly(1-lysine), poly(1-aspartic acid), poly(2-hydroxyethyl-1-aspartamide), etc. blocks] of such copolymers in order to form therapeutic agent containing micelles. Depending on the degree of hydrophilicity/hydrophobicity of the conjugated drug, there may be a need to also attach additional units (e.g., hydrophobic units) to the poly(amino acid) block in order to achieve the amphilicity required for micelle formation.

In other instances, therapeutic agents are physically encapsulated within micelles formed using poly(alkylene oxide)-block-poly(amino acids). Physical encapsulation is commonly carried out through dialysis or emulsion techniques, although spontaneous micelle formation may also occur. For example, in some instances, a therapeutic agent is encapsulated using poly(ethylene oxide)-block-poly(amino acids) conjugates like those described in the prior paragraph. A strong interaction between the conjugated and physically encapsulated therapeutic agents (which are the same) is believed to improve micellar stability.

In other instances, poly(ethylene oxide)-block-poly(amino acids) are used which have a strong affinity for the therapeutic agent. For example, certain poly(ethylene oxide)-block-poly(amino acids) having aromatic structures (e.g., poly(amino acids) such as poly(β-benzyl-1-aspartate), poly(β-benzyl-1-glutamate), etc.) have been used to encapsulate therapeutic agents which also have aromatic structures. A π-π interaction between the aromatic core of the micelles and the aromatic structure within the drug are believed to enhance the stability of such systems.

Other amphiphilic block copolymers, such as poly(ethylene oxide)-block-poly(N-hexyl stearate-1-aspartamide) have also been successfully employed in micelle formation. Furthermore, depending on the amino acid employed, the poly(ethylene oxide)-block-poly(amino acid) copolymer can form polyionic complexes with oppositely charged macromolecules such as DNA or peptides, leading to micellization.

Further information regarding micelles may be found, for example, in Lavasanifar A. et al., "Poly(ethylene oxide)-block-poly(1-amino acid) micelles for drug delivery," *Advanced Drug Delivery Reviews*, 54 (2002), 169-190; Kakizawa Y. et al., "Block copolymer micelles for delivery of gene and related compounds," *Advanced Drug Delivery Reviews*, 54 (2002), 203-222 each of which is incorporated by reference in its entirety.

As noted above, in addition to having one or more therapeutic agent sources, the various internal drug delivery devices of the present invention are also provided with (a) one or more first electrodes, (b) one or more second electrodes, and (c) one or more power sources for applying voltages across the first and second electrodes.

The nature of the applied voltages will vary widely, depending upon on the effect that is desired. For example, in some embodiments, a voltage is applied to at least temporarily retain the therapeutic agent within the device (e.g., via iontophoresis of a charged therapeutic agent in the direction of an internal electrode). In some embodiments a voltage is applied to release the therapeutic agent (e.g., via iontophoresis of a charged therapeutic agent in the direction of an electrode that is external to the therapeutic agent source, or via neutralization of a conductive polymer which leads to expulsion of a charged therapeutic agent from the device). Moreover, in some embodiments, the potential is applied to promote electroporation.

Iontophoretic retention and release can be induced by application of a variety of electrical stimuli including (a) constant current, (b) constant voltage, (c) current scan/sweep, e.g., via a single or multiple sweeps, (d) voltage scan/sweep, e.g., via a single or multiple sweeps, (e) current square waves or other current pulse wave forms, (f) voltage square waves or other voltage pulse wave forms including exponential voltage output pulses, and (g) a combination of different current and voltage parameters.

For electroporation, high voltage pulses are generally used to create the transient pores within cells exposed to the electric field, allowing the cells to be loaded with therapeutic agent (e.g., due to diffusion, migration or both). The density and size of the transient open pores of the cell membrane depend, for example, on the electric field parameters and polarity. See, J. Gehl, *Acta Physiol Scand* 2003, 177, 437-447). This can be used to tailor the entry of various therapeutic agents of various sizes into the cell membranes or into organelles within the cells. Typical voltage pulses for electroporation have a field strength of 50-500 V/cm, more typically 100-200 V/cm, among other ranges, and have a duration that may vary widely, commonly ranging, for example, between 0.0001 ms and 10,000 ms, among other ranges. Single and multiple pulses are commonly employed, with 5 to 20 pulses (e.g., 10 pulses) being typical.

Power sources and power application schemes for use in iontophoretic drug delivery and/or electroporation are well known in the medical device art and will not be discussed further herein. Manufacturers of electroporation equipment include Bridge Technology, Palo Alto, Calif., USA, BTX/Genetronics, San Diego, Calif., USA, Cyto Pulse Sciences, Columbia, Md., USA, E-C Apparatus Corp, Holbrook, N.Y., USA, Invitrogen, Carlsbad, Calif., USA, Jouan, Inc., Winchester, Va., USA, Life Technologies, Gaithersburg, Md., USA, Owl Scientific, Inc., Woburn, Mass., USA, among others.

With respect to the electrodes for use in the present invention, they may be formed form any conductive material suitable for supporting the drug delivery technique employed by the medical device, including iontophoresis and/or electroporation. Examples of conductive materials for electrodes include suitable members of the following, among many others: metals and metal alloys (e.g., stainless steel or gold or platinum, due to their high conductivity, oxidation resistance, and radioopacity, which facilitates visibility of the device during fluoroscopy or the like, or magnesium, which can be left in the tissue where it will eventually oxidize in vivo), conductive polymers, and conductive carbon. Electrodes may take on innumerable shapes, including layers, rods, wires, tubes, blades, grids, among many others.

In some aspects and embodiments, the electrodes of the medical devices of the present invention are configured such that, when the medical device is properly deployed in a subject and a suitable constant or variable voltage is applied across the electrodes, an electric field is directed through a source of therapeutic agent such that the therapeutic agent is driven outward from the device (e.g., in the direction of surrounding tissue).

Specific embodiments in accordance with the present invention will now be described with reference to FIG. 14, which is an exterior view of a balloon catheter 100. Catheter 100 is shown for the purpose of aiding in the understanding of the present invention and a wide variety of other medical devices, including other catheters, are within the scope of the invention. The catheter 100 shown includes a Luer assembly 110 having a Luer port 114 for liquid introduction and a hub 116 for guide-wire 112 introduction and for manipulation of the catheter 100. The Luer assembly 110 allows for access to the catheter lumen, such as the injection of inflation fluids or drugs, or the introduction of a guide wire 112. The balloon catheter 100 illustrated comprises a distal portion 102 that includes an expandable portion 120. The distal portion 102 may be of any desired length.

Figures 2A, 2B:
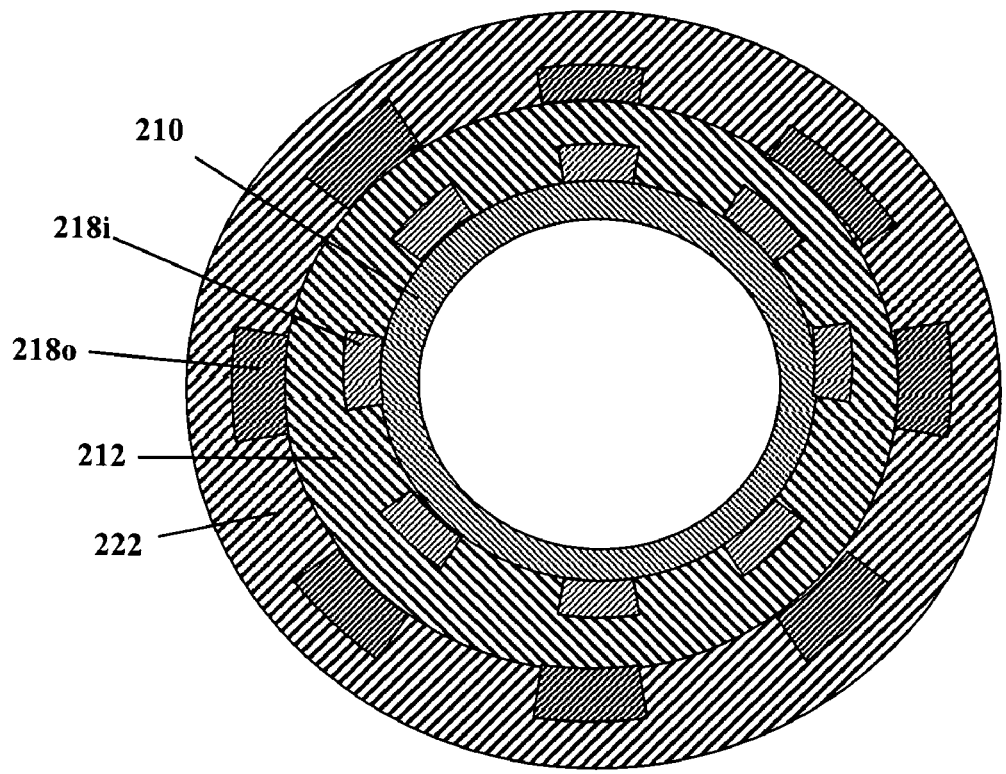
FIG. 2A is a schematic cross-sectional view of the medical device of FIG. 14, in accordance with an embodiment of the present invention.
FIG. 2B is a schematic cross-sectional view of the medical device of FIG. 14, in accordance with another embodiment of the present invention.
Figure 14:
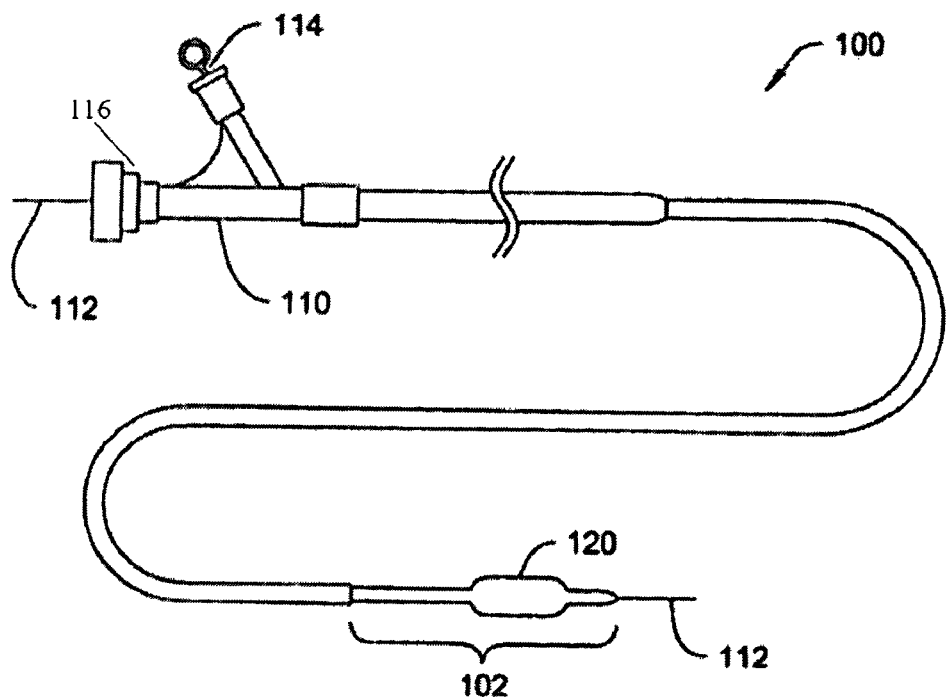
FIG. 14 is an external view of a balloon catheter in accordance with the present invention.

For example, FIG. 2A illustrates a cross sectional view of the expandable portion 120 of an embodiment of the device of FIG. 14, upon insertion and expansion in a lumen created by the surrounding tissue 222 (e.g., a blood vessel) of a subject. FIG. 2A illustrates an expandable medical device substrate 210, such as a balloon, which may be formed from a metallic or non-metallic material such as those described above (e.g., a polyether-polyamide block copolymer substrate such as a PEBAX). Where the substrate 210 is non-conductive and hence unable to efficiently function as an electrode, an inner electrode, for example, in the form of a metal grid 218*i* (or a metal layer 218*i*, as shown in the nearly identical embodiment of FIG. 2C), is provided over the substrate 210. For example, a metal grid or layer may be deposited on the balloon using masking and deposition methods, such as sputter deposition. Provided over the device substrate 210 and inner electrode 218*i*, is a therapeutic-agent-containing polymeric coating 212, such as one containing a charged therapeutic agent and an ion-conductive polymer (e.g., an ion-conductive polymer such as a polyether, a polyamide, a polyether-polyamide block copolymer, or a crosslinked polyether-polyamide blend). Such coatings may be provided using solvent- or thermoplastic-based techniques as described above. Although not illustrated, the surface of the therapeutic-agent-containing polymeric coating 212 can be roughened to increase the interfacial surface area between the coating and the surrounding environment, which may improve transport of the therapeutic agent across the interface. An outer electrode 218*o*, for example, in the form of a metal grid, is provided on the outer surface of the therapeutic-agent-containing polymeric coating 212, for example, by deposition. During drug delivery a power source (not shown) is used to apply a suitable voltage (which may be constant or time-dependent, both in magnitude and in polarity) between the inner and outer electrodes 218*i*, 218*o*. The polarity that is utilized will depend, for example, upon the charge of the therapeutic agent that is to be delivered from the polymeric coating, as well as on whether it is desired to drive the therapeutic agent in the direction of the substrate 210 (to help retain the agent) or whether it is desired to drive the therapeutic agent in the direction of the tissue 222 (to help release the agent).

Figure 2C:
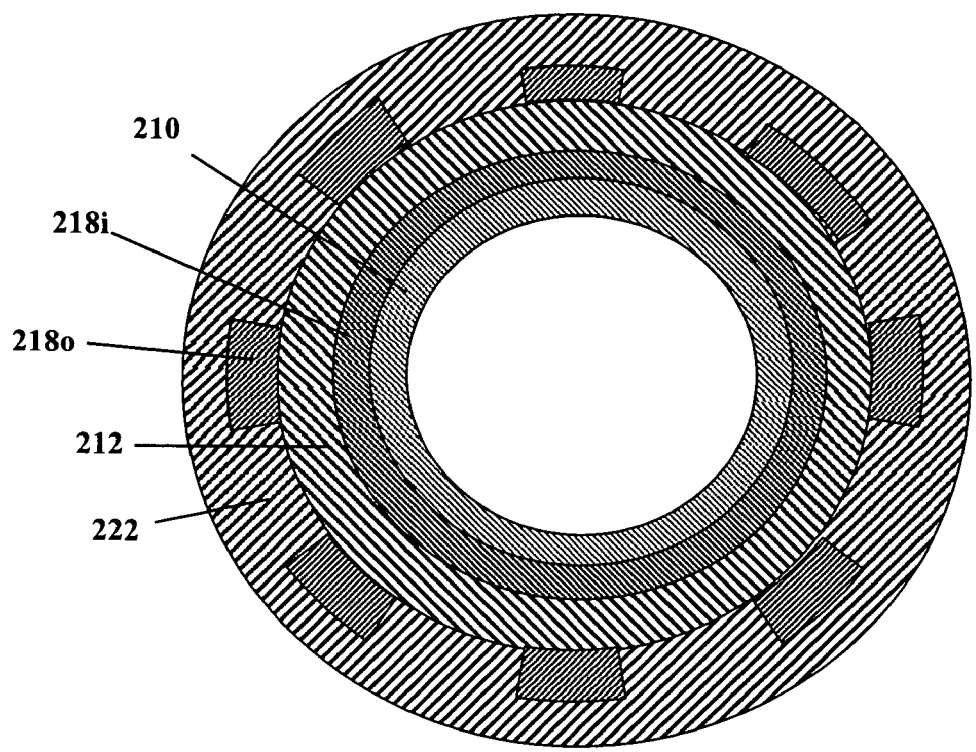
FIG. 2C is a schematic cross-sectional view of the medical device of FIG. 14, in accordance with yet another embodiment of the present invention.
Figure 2D:
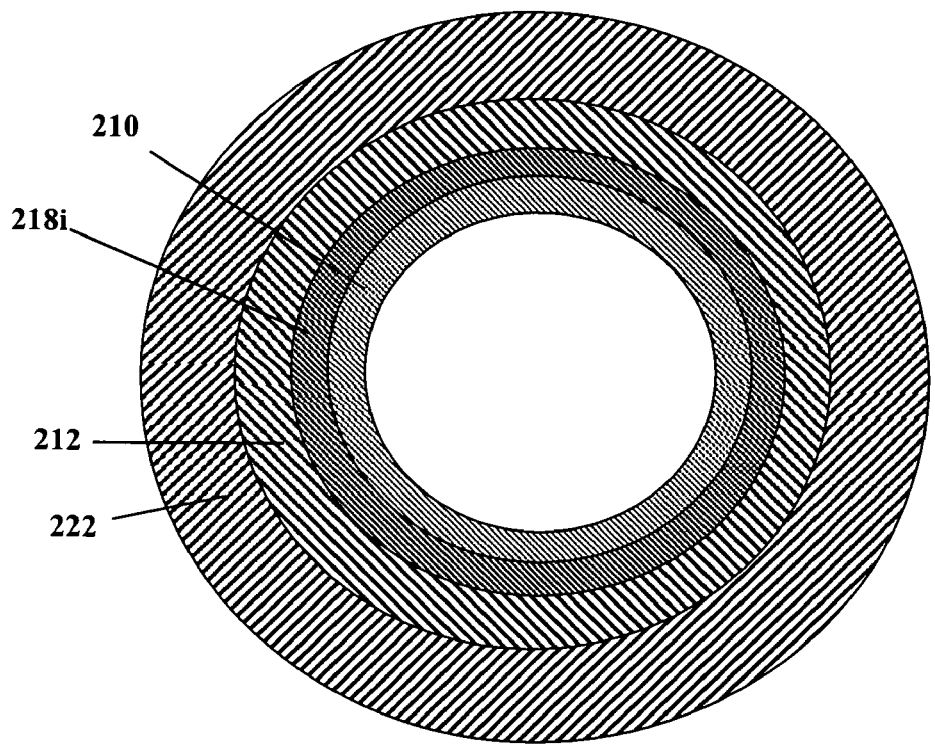
FIG. 2D is a schematic cross-sectional view of the medical device of FIG. 14, in accordance with still another embodiment of the present invention.

In other embodiments, such as that illustrated in FIG. 2D, the therapeutic-agent-containing polymeric coating 212 contains a charged therapeutic agent (e.g., a negatively charged therapeutic agent) and an electrically conductive polymer (e.g., oxidized or super-oxidized polypyrrole). A specific example of a technique by which such a balloon may be constructed follows. With reference to FIG. 2D, a polyether-block-polyamide balloon 210 is at least partially coated with a conductive layer 218*i* such as a gold layer (because the balloon in this instance is not electrically conductive and hence unable to efficiently function as an electrode, e.g., for the electropolymerization step to follow). Polypyrrole is then electropolymerized on the surface of the conductive layer 218*i* (e.g., in the presence of a charged therapeutic agent, which is incorporated in the polypyrrole) to complete the device.

Unlike FIGS. 2A and 2C above, an additional conductive layer 218*o* is not provided at the polypyrrole surface in FIG. 2D (e.g., to avoid shorting, as the polypyrrole is electrically conductive). Instead, an electrolyte (e.g., bodily fluid such as blood) is preferably disposed between the polypyrrole and the counterelectrode. A variety of counterelectrode arrangements are possible. In many embodiments, one or more counterelectrodes are provided within the lumen into which the balloon is inserted. For instance, one or more counterelectrodes may be mounted on the surface of the balloon by placing an insulating layer between the polypyrrole and the counterelectrode. This insulating layer may be, for example, a porous layer or a ion transfer membrane that covers the entire balloon (whereas the counterelectrode may be a metal grid, wrapped wire, etc., to allow therapeutic agent to be released), or the insulating layer may be provided in the form of one or more small patches on the balloon surface (e.g., each with a counterelectrode region on its surface), thereby allowing the polypyrrole to be directly exposed to the bodily fluid. As further example, one or more counterelectrodes may be provided at the surface of the catheter at a position that is proximal (or distal) to the balloon (e.g., a gold markerband crimped around the proximal shaft could further function as a counterelectrode), a guidewire may be used as a counterelectrode, and so forth.

Figure 1B:
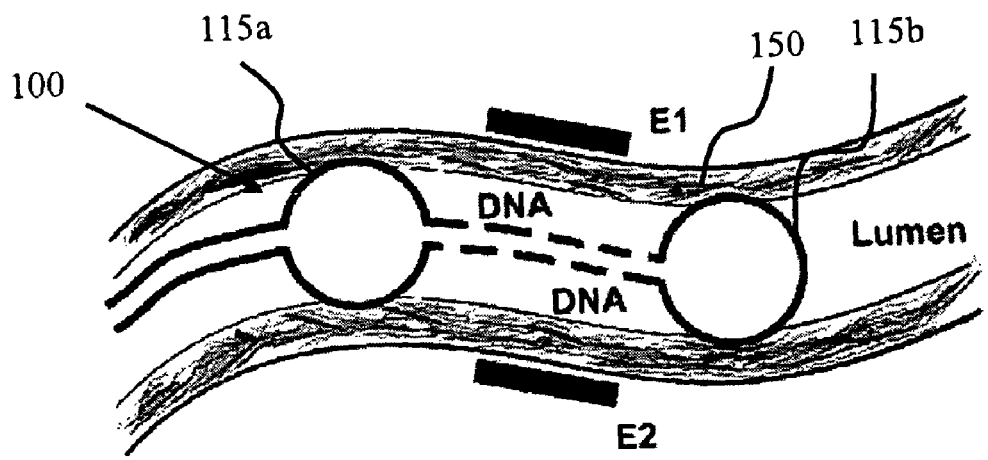
FIG. 1B is a schematic cross-sectional view illustrating a method of delivering a therapeutic agent to body lumen wall via electroporation, in accordance with the prior art.

Note that, unlike a porous balloon design, such as that illustrated in FIG. 1A (which makes the balloon unsuitable as an angioplasty balloon as it is only suited for low pressures), balloons like those discussed above can both be used for angioplasty as well as for drug delivery.

Electropolymerization of electropolymerizable monomers such as pyrrole to form a polymer film with incorporated doping (therapeutic agent) ions, can be carried under a variety of d.c. and a.c. electrochemical conditions including the following: (a) constant current, (b) constant voltage, (c) current scan/sweep, e.g., via a single or multiple sweeps, (d) voltage scan/sweep, e.g., via a single or multiple sweeps, (e) current square waves or other current pulse wave forms, (f) voltage square waves or other voltage pulse wave forms, and (g) a combination of different current and voltage parameters. The polarity of applied current and voltage parameters can be monophasic or biphasic, with the electrochemical windows/ranges provided, as applicable, from cathodic to anodic regions, and adjusted for required reduction/oxidation processes of the electropolymerizable species. The electrochemical techniques that use some of the listed conditions are known under different names. Common terminology for these methods include, for example, potentiostatic, potentiodynamic, cyclic voltammetry, potential square wave, potential square step, potential scan/hold, square wave voltammetry, galvanostatic, galvanodynamic, galvanic cyclic, galvanic square wave, and so forth.

In some aspects and embodiments, the electrodes of the medical devices of the present invention may be configured such that, when the medical device is properly deployed in a subject and a suitable constant or variable voltage is applied across the electrodes, an electric field is directed into the tissue of the subject. As a result, a number of desirable effects may be achieved. For example, charged therapeutic agent may be driven into the tissue (e.g., in connection with iontophoresis), transient pores may be created in the cell membranes and/or organelles of the cells of the tissue (e.g., in connection with electroporation), and so forth.

One method for creating such an electric field is to configure the first and second electrodes such that, when the medical device is properly deployed in a subject, the tissue of the subject (and, in certain embodiments, a source of therapeutic agent as well) is positioned between the electrodes.

In some aspects and embodiments of the invention, this is achieved by positioning one or more inner electrodes at or near the surface the medical device, and by positioning one or more outer electrodes within or beyond the tissue for which treatment is desired.

For example, like FIGS. 2A, 2C and 2D, FIG. 2B illustrates a cross sectional view of the expandable portion 120 of an embodiment of the device of FIG. 14, upon insertion and expansion in a lumen created by the surrounding tissue 222 of a subject. FIG. 2B illustrates an expandable medical device substrate 210, such as a balloon, which may be formed from a metallic or non-metallic material such as those described above (e.g., a polyether-polyamide block copolymer substrate such as a PEBAX). Where the substrate 210 is non-conductive and hence unable to efficiently function as an electrode, a first electrode, for example, in the form of a tube or a metal grid 218, is provided over the substrate 210. Provided over the device substrate 210 and first electrode 218, is a therapeutic-agent-containing polymeric coating 212, such as one containing a charged therapeutic agent and an ion-conductive polymer. If desired, the surface of the therapeutic-agent-containing polymeric coating 212 can be roughened to increase the interfacial surface area between the coating and the surrounding environment. A second electrode (not shown) is provided on the skin of the subject. Electrical contact can be enhanced as known in the iontophoresis art, using conductive gels, creams, and so forth. The entire assembly is positioned within a lumen created by surrounding tissue 222 of a subject (e.g., a blood vessel). During drug delivery a power source (not shown) is used to apply a suitable constant or time-dependent voltage between the first and second electrodes. As above, the polarity that is utilized will depend, for example, upon the charge of the therapeutic agent that is to be delivered from the polymeric coating, as well as upon whether it is desired to retain or release the therapeutic agent.

Figure 3:
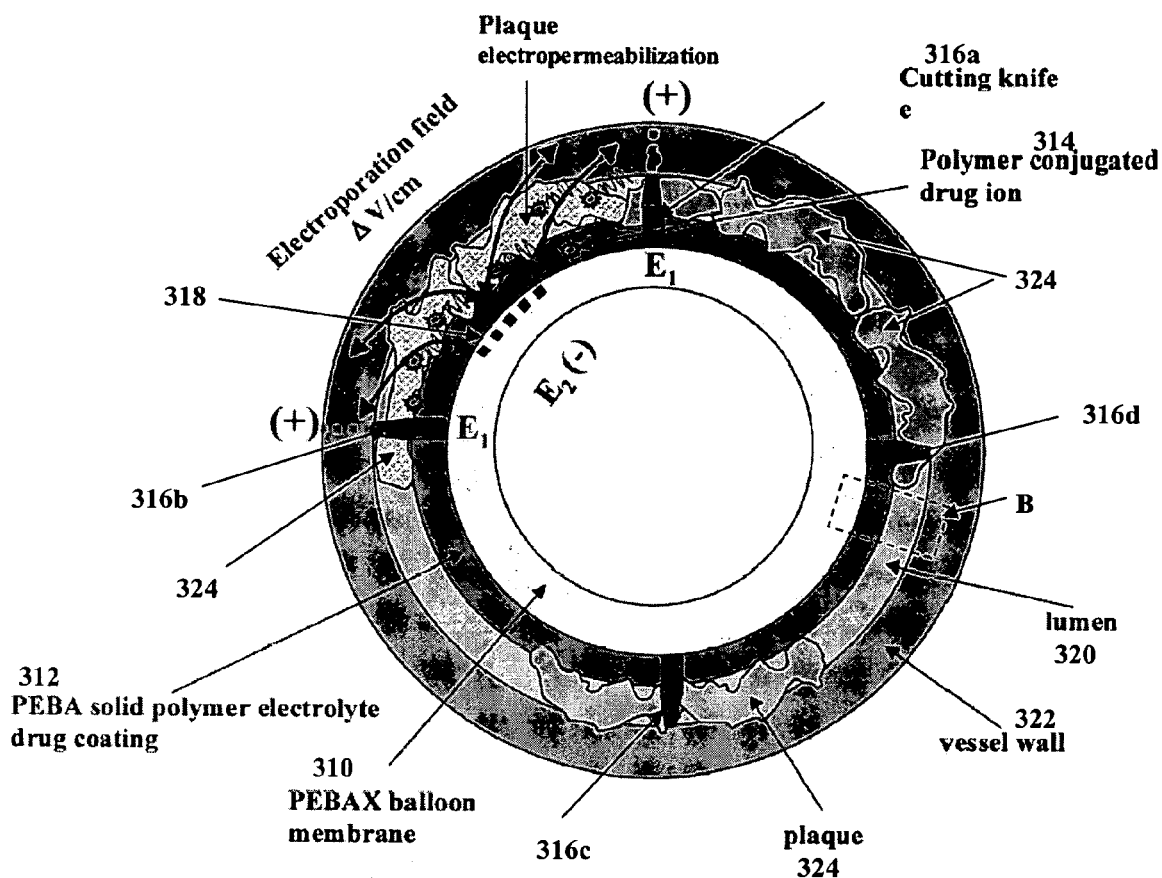
FIG. 3 is a schematic cross-sectional view of a drug delivery balloon, in accordance with another embodiment of the present invention.

Another embodiment of the invention by which the tissue of a subject may be positioned between first and second electrodes is shown in FIG. 3, which illustrates a cross sectional view of a medical device disposed within a lumen 320 created by surrounding tissue 322. Numerous plaque deposits 324 are found on the inner surface of the vessel wall 322. The medical device contains an expandable tubular medical device substrate, such as a stent body or a balloon 310, which may be formed from a variety of materials such as those described above (e.g., a polyether-polyamide block copolymer substrate such as a PEBAX). The balloon 310 is provided with a source of therapeutic agent, for example, a therapeutic-agent containing polymeric region such as one containing charged drug molecules 314 dispersed within an ion-conductive polymeric coating 312. A first electrode 318 is provided beneath and in electrical contact with the coating 312. Although a single first electrode 318 is shown, multiple first electrodes may be employed, for example spaced at regular intervals around the circumference of the balloon 310. As above, the surface of the coating 312 can be roughened to increase the interfacial surface area between the coating and the surrounding environment, which may improve transport of the therapeutic agent across the interface. The outer surface of the balloon 310 is provided with cutting blades 316a-d, which can be formed from a variety of conductive materials, for example, from stainless steel or another suitable metal, on a non-conductive material, such as a diamond material, may be provided with a conductive coating. Note that the cutting blades can take on a number of configurations, including those known in the cutting balloon art (e.g., longitudinally linear configurations, spiral configurations, etc., among many others). In embodiment of the present invention shown, the cutting blades 316a-d also function as second electrodes. Hence, the primary requirements of the cutting blades 316a-d are that they be capable of cutting and penetrating tissue, and that they be sufficiently conductive to provide an electric field that is suitable for therapeutic agent delivery.

Although not apparent from FIG. 3, although the tips of the cutting blades 316a-d are in electrical contact with the surrounding tissue, the sides of the blades 316a-d, particularly those portions adjacent the ion-conductive polymeric coating 312, may be provided with layer of insulating material, for example, a diamond layer or non-conducting polymer layer, among many others.

As a specific example, blades may be mounted on the balloon as is typical in the cutting balloon art. A conductive layer such as a gold layer is then deposited (e.g., by sputtering) over the structure, while masking the blades as well as portions of the balloon immediately adjacent to the blades (in order to prevent direct electrical contact between the blades and the gold layer). Alternatively, non-conductive blades such as diamond blades, with a conductive coating such as a gold coating, may be employed. An insulating layer can be provided over the blades (e.g., a diamond-like coating may be deposited, for instance, using laser vapor deposition). By shielding the tips of the blades, the blades become insulated with the diamond-like coating, except at the tips. A conductive layer such as a gold layer is then deposited over the structure, while masking the blade tips as well as portions of the blades immediately adjacent to the blade tips (in order to prevent direct electrical contact between the conductive blade tips and the gold layer).

Subsequently, an ion-conductive polymeric layer, along with a therapeutic agent, is then deposited on top of the conductive (e.g., gold) layer. Depending on the embodiment, once the therapeutic agent containing polymeric layer is established, the blades or blade tips may be unmasked to complete the device.

In the embodiment illustrated in FIG. 3, the balloon 310 has been inflated such that the tips of the cutting blades 316a-d penetrate various plaque deposits 324. A power source (not shown) is then used to place the cutting blade electrodes 316a and 316b at a first potential E1 and the electrode 318 at a second potential E2, which is negative relative to the first potential E1, thereby creating an electric field having a main vector that is transverse to the axis of the catheter (and lumen). Consequently, the charged drug 314 (which is negatively charged in the embodiment illustrated), experiences an electrical driving force which transports the drug outward into the plaque deposit 324 as illustrated. Moreover, by applying a series of high voltage pulses, transient pores may be created in the membranes of cells exposed to the electric field, allowing the cells to be loaded with therapeutic agent. The potential difference during such voltage pulses may be established, for example, between the electrodes that are provided beneath the coating 312 (e.g., electrode 318) and the tissue penetrating electrodes (e.g., cutting blade electrodes 316(a), 316(b)), as in the above iontophoresis step. Alternatively, the potential difference for electroporation may be established between adjacent tissue penetrating electrodes, such as electrode 316(a) and 316(b).

Of course, by switching the polarity of the electrodes, positively charged therapeutics can be subjected to outward driving forces. Moreover, both positive and negative therapeutic agents can both be electrically transported into surrounding tissue by first applying a voltage across the electrodes that has a first polarity, and then switching the polarity of the applied voltage, with electroporation pulses being optionally provided after driving each therapeutic agent into tissue, as desired.

Thus, in contrast with current electroporation balloon systems, such as that illustrated in FIG. 1A, this design (as well as certain others described herein) creates a main electrical vector that is oriented transversely with respect to the axis of the device and into surrounding tissue. Moreover, if desired, this design (as well as certain others described herein) allows for only a part of the vessel circumference to be treated with a drug infusion, for example, by selecting which electrode(s) are to be operated. In some embodiments, temperature sensors may be provided at the outer surface of the device to sense the position of one or more regions requiring treatment (e.g., the position of vulnerable plaque), and subsequently providing treatment (e.g., iontophoresis and/or electroporation) only in these regions or providing additional treatment in these regions.

Other than cutting blades, a variety of other penetrating members may be used in the present invention. Other examples of penetrating members include tubular protrusions such as those described in U.S. Pat. No. 6,210,392 to Vigil et al., which is incorporated by reference in its entirety.

As another alternative, instead of (or in addition to) using macro-sized penetrating electrodes such as cutting blades or other protrusions, which penetrate (i.e., pierce) the vessel wall or deflect the vessel wall (e.g., creating a temporary indentation in the vessel wall) only at a few points, other embodiments of the invention utilize arrays of electrically conductive, tissue penetrating micromembers (i.e., members that are less than about 10 microns (micrometers) in penetration length), such as microblades and microneedles. In addition to puncturing the tissue at many, many locations, such members may require much less force to penetrate tissue than the larger sized cutting blades and other protrusions. One will also be able to utilize devices that are very small.

Figure 4:
FIG. 4 is a perspective view of an ordered array of tissue penetrating members, for use in various embodiments of the present invention.

Microblades and microneedles are known and may be made by a variety of technologies, for example, such as LIGA ("lithographic galvanoformung abformung," meaning lithography, electroforming, molding) and other metal MEM (micro-electro-mechanical) technologies. For example, FIG. 4 illustrates an ordered array of penetrating members 416 created using LIGA technology. As noted above, materials for such members may include corrosion resistant materials such as stainless steel, gold or platinum, or materials that will degrade in vivo, such as magnesium.

Microneedles can also be made out of carbon nanotubes, which have been shown to be able to puncture through several cells, without actually damaging the membrane. As carbon nanotubes are highly conductive, they are suitable for use in the devices of the invention. Being able to penetrate through the cell membrane to bring the second electrode to the opposite side without actually damaging the cell is of course highly desirable.

Examples of carbon nanotubes include single-wall carbon nanotubes and multi-wall carbon nanotubes (which term embraces so-called "few-wall" carbon nanotubes). Specific examples of nanotubes include single wall carbon nanotubes (SWNTs), which have inner diameters ranging from 0.25 nanometer to 5 nanometers, and lengths up to 10's of micrometers, and multi-wall carbon nanotubes, which have inner diameters ranging from 2.5 nanometers to 10 nanometers, outer diameters of 5 nanometers to 50 nanometers, and lengths up to 10's of micrometers.

An example of a technique which can be used to provide a substrate with carbon nanotubes having a relatively perpendicular orientation follows. First, aligned carbon nanotubes are grown on within catalyst-lined island trenches of a silicon wafer. This structure is then overcoated with an epoxy polymer (e.g., by spin coating), followed by planarization of the structure using chemical mechanical polishing (CMP) to create distinct islands with oriented carbon nanotubes of uniform length. These islands are removed, for instance, using a $XeF_2$ plasma, and a portion of the epoxy is removed in an oxygen plasma. The resulting islands, which contain carbon nanotubes that partially protrude from epoxy, are placed on a layer, such as an indium layer, which is softened by heating so that the carbon nanotubes become embedded in the indium layer. This structure is then exposed to another oxygen plasma so as to remove the remaining epoxy. See, e.g., T. A. El-Aguizy et al., "Transplanting carbon nanotubes," *Applied Physics Letters*, 85(24) pp. 5995-5997. Dec. 13, 2004, which is incorporated by reference in its entirety.

In the present invention, the islands may be embedded in a biocompatible substrate. In this regard, it is noted that indium is a biocompatible material and is used as a replacement for zinc in dental alloys. Indium is also naturally self-passivating, having a native indium oxide layer that is typically 80-100 Angstroms in thickness. Hence, a strip of indium may be used as a biocompatible substrate. As another example, a layer of indium (e.g., 0.001" to 0.004") may be deposited (e.g., by sputtering) on top of another metallic or non-metallic material (e.g., platinum, among many other possibilities). The islands may be embedded in the indium layer by heating. If desired, the substrate with embedded islands may be subjected to further processing (e.g., epoxy removal, etc.) prior to being attached to an underlying medical device substrate (e.g., a balloon or other expandable member), for instance, using an adhesive.

Figure 5:
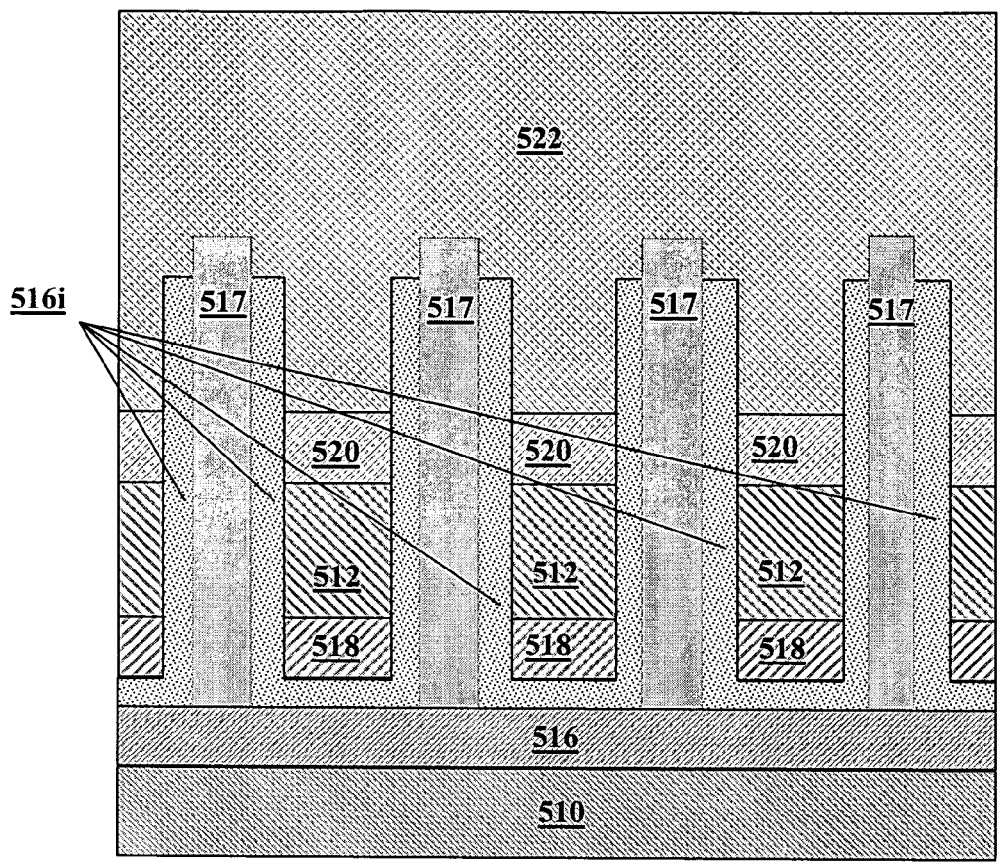
FIG. 5 is a schematic cross-sectional partial view of a medical device that contains an array of microneedles, in accordance with another embodiment of the present invention.

An embodiment of a structure containing microneedles is illustrated schematically in partial cross-section in FIG. 5. The area of the cross section of FIG. 5 is analogous, for example, to that of area B in FIG. 3 (note, however, the curvature of the balloon and overlying layers is not illustrated). FIG. 5 illustrates a substrate such as a balloon 510, a conductive layer 516 on the balloon, conductive needles 517 formed on or from the conductive layer 516, an insulating layer 516i disposed over the conductive layer 516 and portion of the needles 517, leaving the tips of the needles 517 exposed, a conductive electrode layer 518, and a therapeuticagent-containing layer, such as polymeric layer 512 containing a charged drug. FIG. 5 also illustrates a lumen 520 defined by surrounding tissue 522.

Figure 6A:
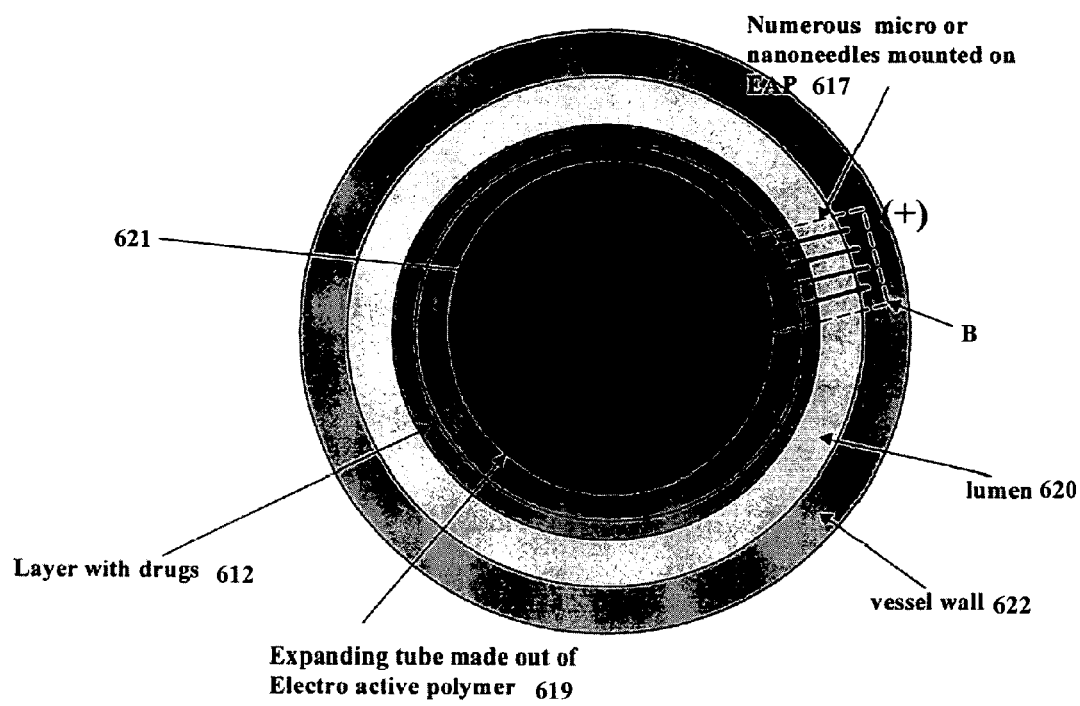
FIG. 6A is a schematic cross-sectional view of a medical device disposed within a body lumen, in accordance with another embodiment of the present invention.
Figure 6B:
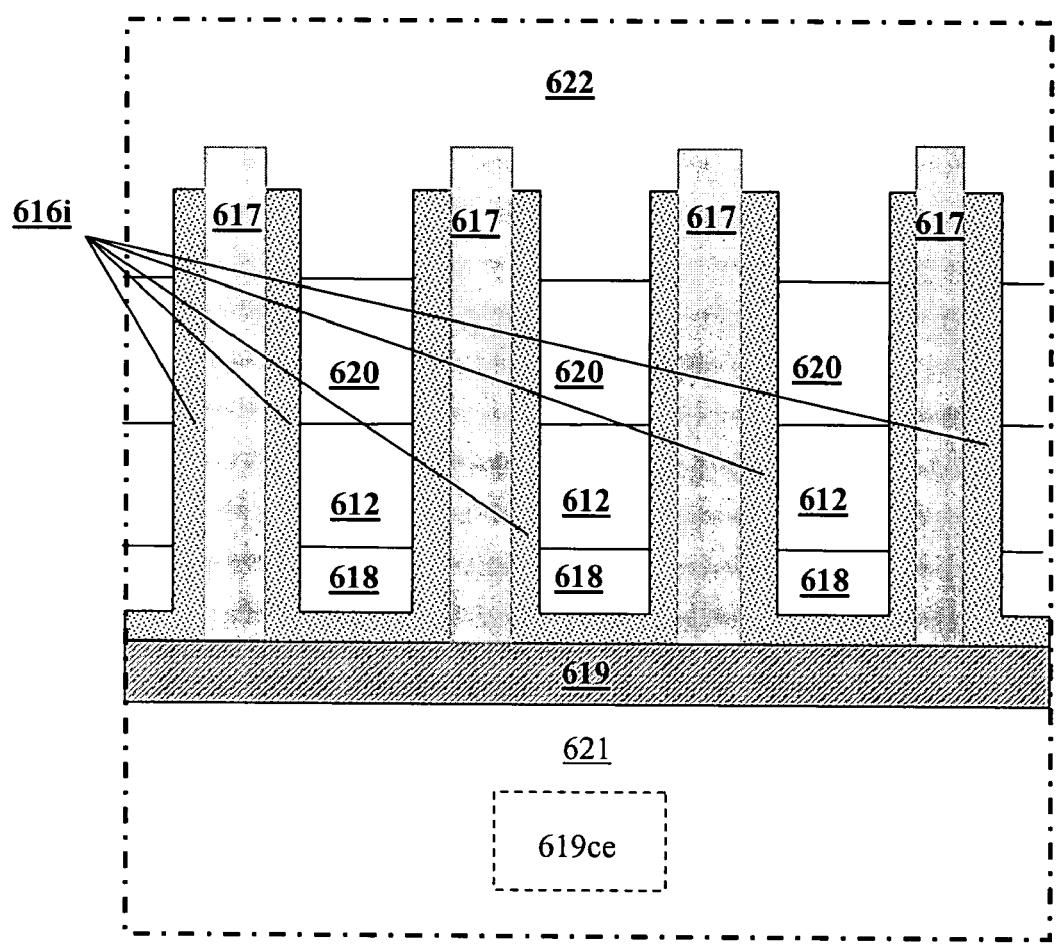
FIG. 6B is a detailed view of area B in FIG. 6A.

FIG. 6A is a schematic, cross-sectional view of a medical device in accordance with yet another embodiment of the invention, which is disposed in a lumen 620 formed by surrounding tissue, such as a vessel wall 622. FIG. 6B is a detailed view of area B in FIG. 6A. The medical device substrate in these figures includes an expanding region 619 (e.g., a tubular region) formed from an electroactive polymer material, such a conductive polymer (e.g., polypyrrole), which does not obstruct flow (e.g., blood flow) due to its tubular nature. During operation, a voltage is applied across the expanding region 619 and a counter-electrode 619ce (which is positioned in the bloodstream 621, in the embodiment shown), which is sufficient to oxidize or reduce the conductive polymer in the expanding region 619, thereby expanding the expanding region 619 as is known in the art. Taking an oxidizable polymer such as polypyrrole as an example, and without wishing to be bound by theory, it is believed that the applied potential results in the oxidation of the conductive polymer such that it takes on a positive charge. In response, anions from the blood 621 are drawn into the expanding member 619, along with their hydration shells, causing the member 619 to swell.

The remainder of the device is much like that of FIG. 5 above, and includes conductive needles 617 in contact with conductive expanding member 619, and an insulating layer 616i disposed over the conductive expanding member 619 and portion of the conductive needles 617, leaving the tips of the needles 617 exposed. The device further includes a conductive electrode layer 618 and a polymeric layer 612 containing a charged drug. A voltage is applied across the electrode 618 and the conductive needles 617 (e.g., via the conductive polymer), providing a driving force for the transport of charged drugs from the polymeric layer 612, through the lumen 620, and into the vessel wall 622. Moreover, by applying a series of high voltage pulses, transient pores may be created in the membranes of cells exposed to the electric field, allowing the cells to be loaded with the drug.

FIGS. 8A-8D are schematic, partial cross-sectional views illustrating the use of a CTO (chronic total obstruction) device 810 in accordance with an embodiment of the invention. The device 810 illustrated includes an elongated shaft region 810s and a flared region 810e positioned at the distal end of the shaft region 810s. At the distal end of the elongated region are provided numerous conductive blades or needles 817.

Figure 8A:
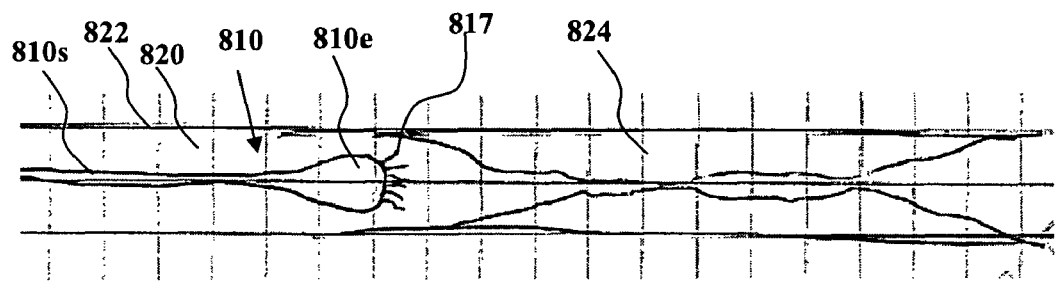
FIGS. 8A-8D are schematic, partial cross-sectional views illustrating the use of a CTO device, in accordance an embodiment of the present invention.
Figure 8B:
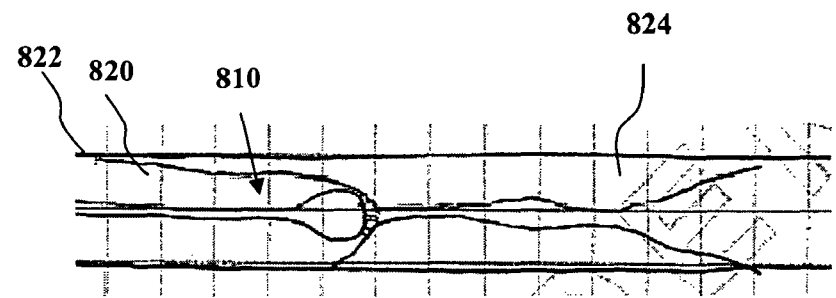
Figure 8C:
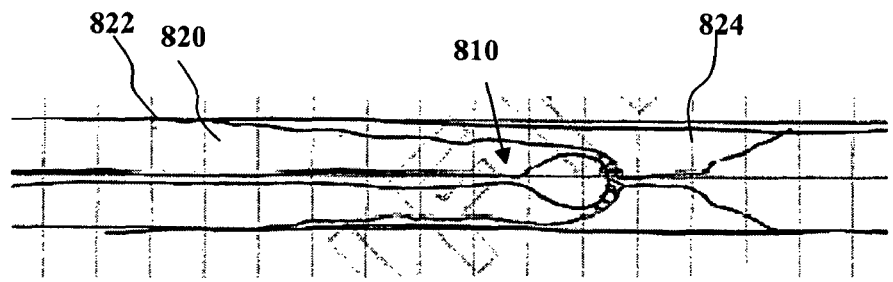
Figure 8D:
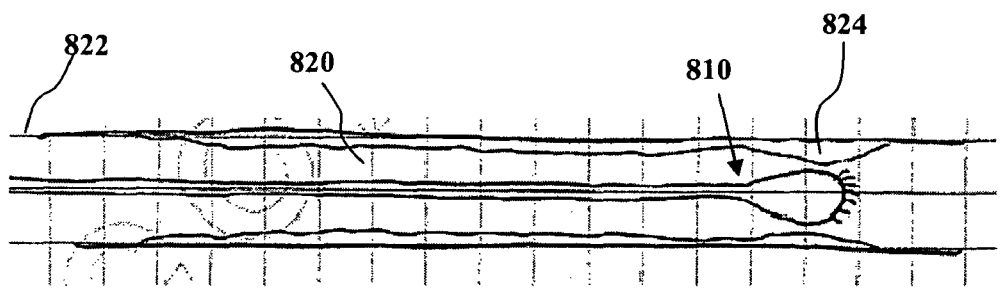
Figure 8E:
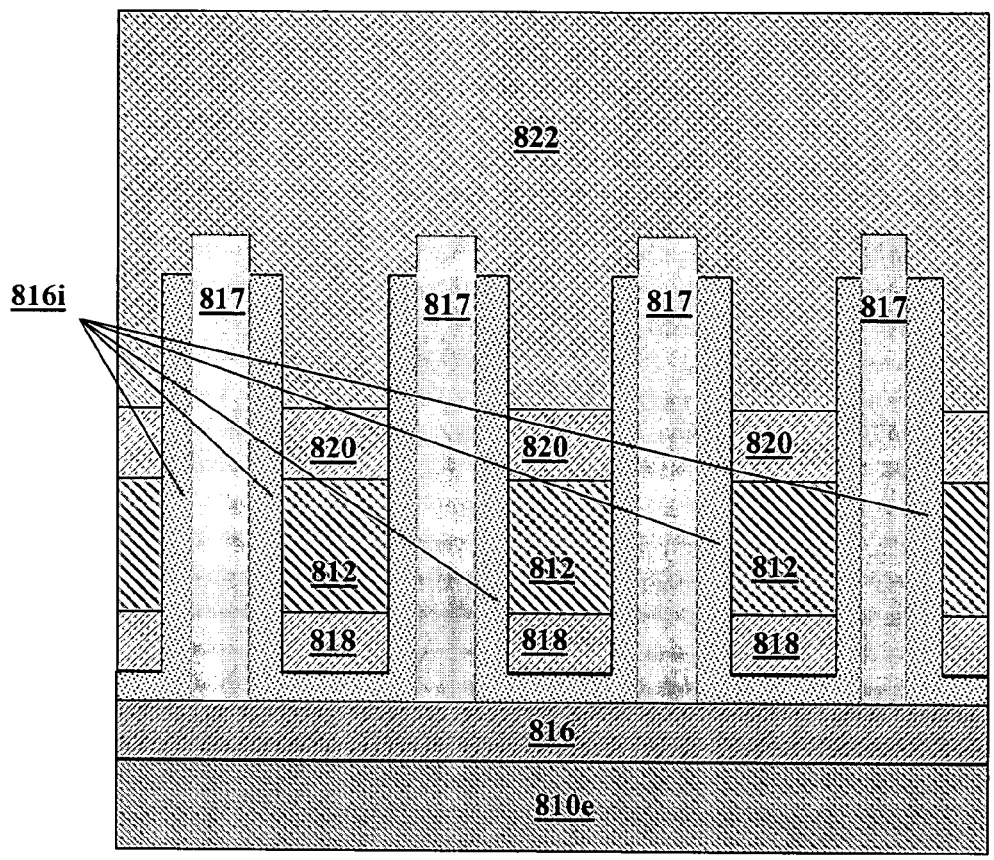
FIG. 8E is a detailed cross-sectional view of a portion of FIG. 8B.

The construction of the device 810 is better understood with reference to FIG. 8E. The area of the cross section of FIG. 8E corresponds to an area taken from the distal end of the expanded region 810e where it engages the obstruction, for example, plaque 824. FIG. 8E illustrates a substrate corresponding to a portion of the flared region 810e at the distal end of the CTO device, a conductive layer 816 on the substrate 810e, conductive needles 817 are formed on or from the conductive layer 816, and an insulating layer 816i is disposed over the conductive layer 816 and a portion of the needles 817, leaving the tips of the needles 817 exposed. Further, a conductive electrode layer 818, and a polymeric layer 812 containing a charged drug are provided. The needles 817 are engaged with the plaque (see also, e.g., FIG. 1B), and a portion of the lumen 820 may lie between the polymeric layer 812 and the plaque 824 as shown.

During operation, the CTO device 810 is inserted through a lumen 820 formed by a vessel wall 822. The device 810 is advanced until obstructing plaque 824 is reached, at which point the needles 817 penetrate the plaque 824 as illustrated in FIGS. 8B and 8E. At this point, a voltage is applied between (a) the electrode layer 818 and (b) the conductive layer 816 and needles 816 of the device 810. In the embodiment illustrated, a charged therapeutic agent, such as a vasodilating agent or a plaque removing agent, is disposed within the polymeric region 812. The voltage applied is of appropriate magnitude and polarity such that the drug is driven from the polymeric layer 812 and into the plaque 824. Subsequent to or concurrent with this iontophoresis process, a voltage scheme suitable to cause electroporation may also be applied to enhance drug delivery.

The CTO device 810 is then retracted slightly, if desired, and advanced further down the lumen until additional obstructing plaque 824 is reached, at which point the needles 817 again penetrate the plaque 824 as illustrated in FIG. 8C. An appropriate voltage is again applied across the electrode layer 818 and the conductive layer 816 and needles 816 of the device 810, clearing further plaque 824, until the device 810 clears the plaque as illustrated in FIG. 8D.

Note that in this particular case, the therapeutic agent employed is relatively fast acting. Of course, in the event that a therapeutic agent is selected that takes effect over a period or hours or even days. The CTO device 810 may be completely withdrawn between steps.

In contrast to treating obstructions, other devices in accordance with the present invention may be used to treat vascular enlargements. For example, in one presently known method for the treatment of an aneurysm, a physician places a catheter at the mouth of the aneurysm, and a coil, such as a Guglilmi detachable coil (GDC), is then inserted through the catheter and into the aneurysm. In the case of the GDC, the coil is a soft platinum coil that is soldered to a stainless steel delivery wire. When the coil is properly positioned within the aneurysm, a small current is applied to the delivery wire, dissolving the same at a position proximal to the platinum coil by means of electrolysis. Once electrolysis occurs, the delivery wire can be removed leaving the coil in place.

Figure 9A:
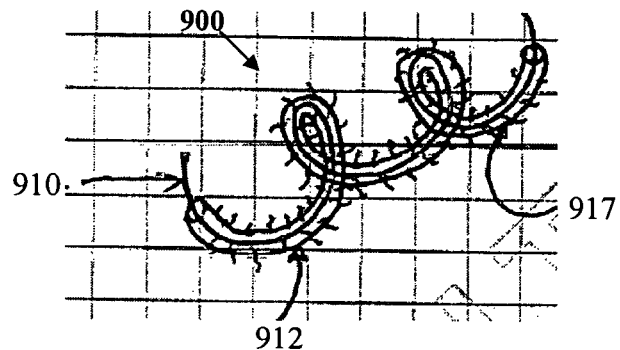
FIG. 9A is a schematic perspective view of an aneurysm filler device, in accordance with an embodiment of the present invention.
Figure 9B:
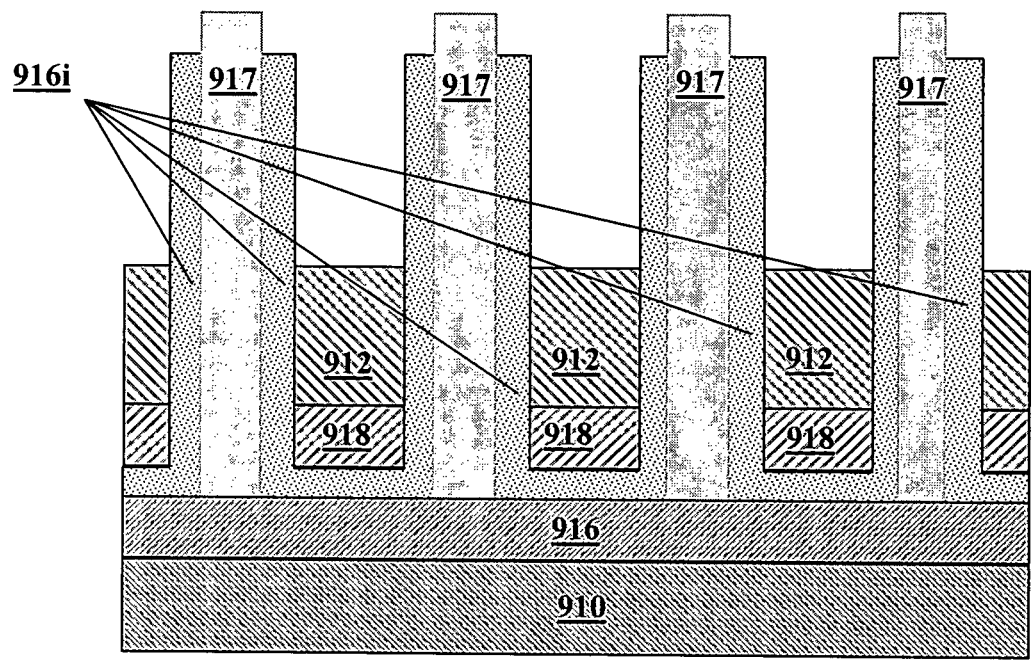
FIG. 9B is a schematic partial cross-sectional view the device of FIG. 9A.

FIG. 9A is a schematic view of a aneurysmal treatment device 900 in accordance with the present invention, which contains a metal coil 910 having a sleeve that surrounds the coil, and which contains, inter alia, a polymeric layer 912 containing a drug (e.g., a charged clotting agent) and numerous conductive needles 917. The construction and operation of the device 900 is better understood with reference to the partial cross-sectional view of FIG. 9B. The area of the cross-section of FIG. 9B corresponds to an area taken from the outer surface of the device 900 of FIG. 9A. As seen from FIG. 9B, the metal coil 910 is surrounded by a sleeve that includes an inner conductive layer 916 (e.g., in the form of a conductive tube) and conductive needles 917, which are formed on or from the conductive layer 916. An insulating layer 916i is disposed over the conductive layer 916 and a portion of the needles 917, leaving the tips of the needles 917 exposed. Further, a conductive electrode layer 918 and polymeric layer 912 are provided over the insulating layer 916i between needles 917.

During operation, the device 900 is inserted into an aneurysm, whereupon a voltage is applied between (a) the electrode layer 918 and (b) the metal coil 910, conductive layer 916 and needles 916 (all of which are conductive). In the embodiment illustrated, a charged therapeutic agent (e.g., a clotting agent), is disposed within the polymeric region 912, and the voltage that is applied is of appropriate magnitude and polarity such that the drug is driven from the polymeric layer 912 and into aneurysm. Subsequent to or concurrent with this iontophoresis process, a voltage scheme suitable to cause electroporation may also be applied to enhance delivery.

Figure 10A:
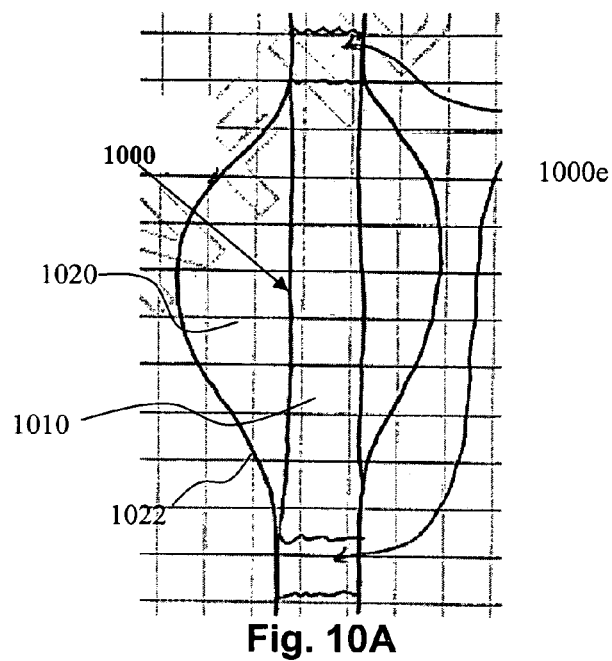
FIG. 10A is a schematic partial cross-sectional view, illustrating an aortic aneurysm graft disposed within an aortic aneurysm.

Turning now to FIG. 10A, this figure is a schematic partial cross-sectional view illustrating an aortic aneurysm graft 1000 disposed within an aneurysm 1020 that is formed in the aortic wall 1022. The graft 1000 includes a tubular substrate 1010, which bridges the aneurysm 1020. The ends 1000e of the graft 1000 are surrounded by and in close contact with the aortic wall 1022.

Figure 10B:
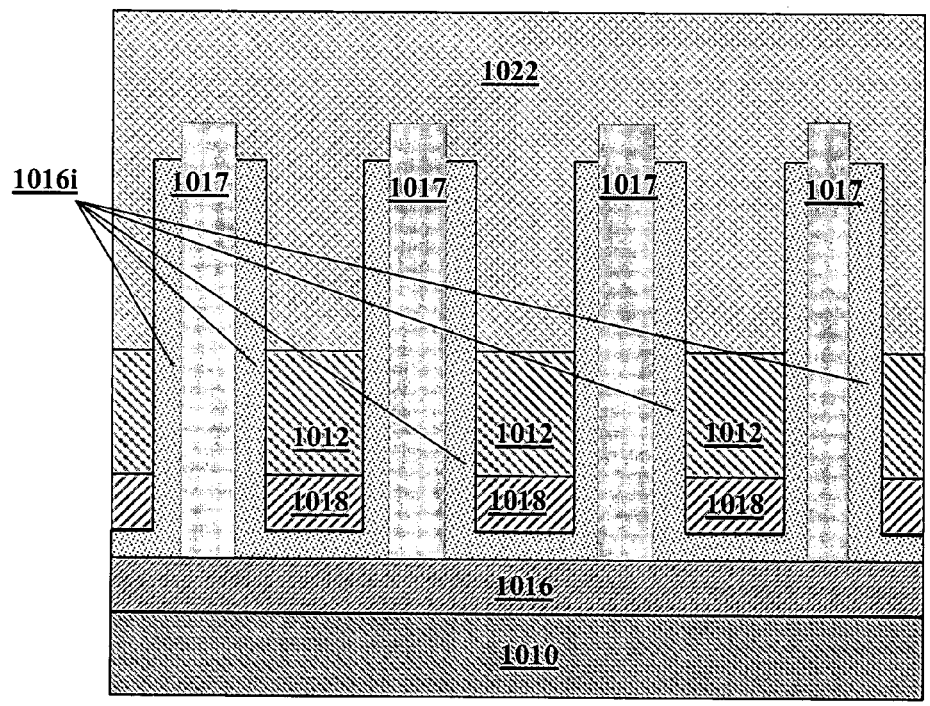
FIG. 10B is a schematic cross-sectional view of a portion of one of the ends of FIG. 10A.

The construction of end regions 1000e of the device 1000 is better understood with reference to FIG. 10B. The area of the partial cross-section of FIG. 10B corresponds to an area taken at one of the end regions 1000e where it engages the aortic wall 1022. FIG. 10B shows the substrate 1010 of the graft 1000, which is coated with a conductive layer 1016. Conductive needles 1017 are formed on or from the conductive layer 1016, and an insulating layer 1016i is disposed over the conductive layer 1016 and a portion of the needles 1017, leaving the tips of the needles 1017 exposed. Further, a conductive electrode layer 1018, and a polymeric layer 1012 containing a charged drug are provided. The needles 1017 are engaged with the aortic wall 1022.

Once the graft is properly positioned within the aorta, a voltage is applied between (a) the electrode layer 1018 and (b) the conductive layer 1016 and needles 1016. In the embodiment illustrated, a charged therapeutic agent, such as a growth factor, is disposed within the polymeric region 1012, and the voltage applied is of appropriate magnitude and polarity such that the drug is driven from the polymeric layer 1012 and into the aortic wall 1024. Subsequent to or concurrent with this iontophoresis process, a voltage scheme suitable to cause electroporation may also be applied to enhance delivery.

Figure 7:
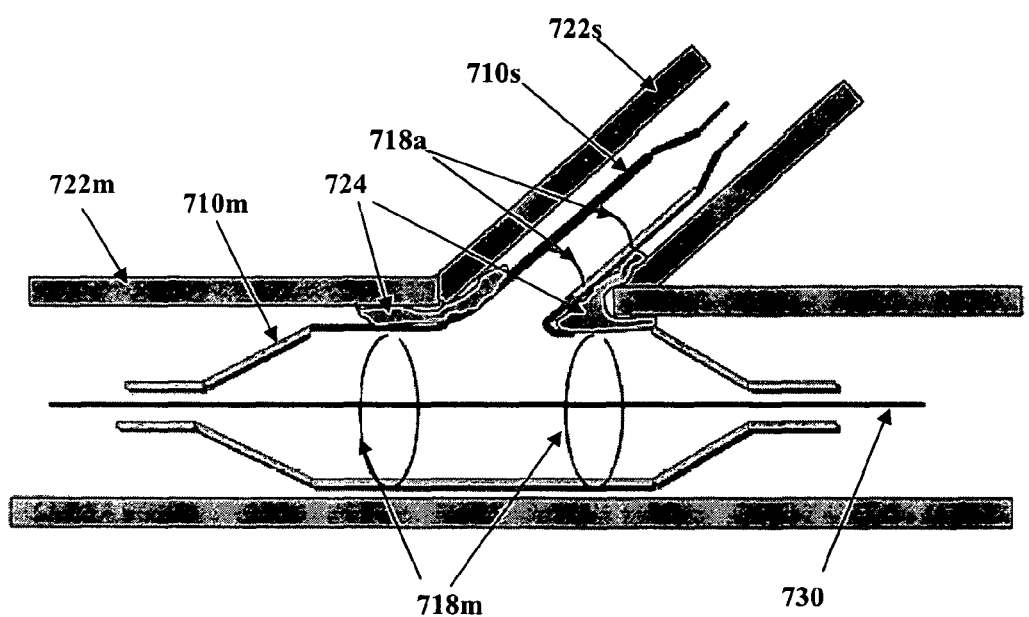
FIG. 7 is a schematic partial cross-sectional view of a balloon device for introduction of therapeutic agent to a bifurcation site, in accordance with another embodiment of the present invention.

Other embodiments of the invention do not require tissue penetration to provide an electrical field that is directed into tissue. One example of such a configuration is shown in the partial cross-sectional view of FIG. 7, which illustrates a medical device in accordance with the present invention disposed at a bifurcation site, which contains a main vessel 722m and a side vessel 722s, with plaque deposits 724 located at the intersection of the vessels 722m, 722s. The device includes a main balloon 710m with a side branch 710s, which are both inflated such that they occupy the lumens of the main vessel 722m and side vessel 722s, respectively. Prior to inflation, the device may be tracked over a guide wire 730, as is known in the art. The main balloon 710m, the side branch 710s, or both, are provided, at least in the vicinity of the plaque 724, with a polymeric layer (not separately illustrated) that contains a charged drug. The main balloon 710m is provided with main balloon electrodes 718m, which may be electrically biased concurrently or independently of one another, and the side balloon 710s is provided with side balloon electrodes 718s, which may be biased concurrently or independently.

Drug delivery is enhanced by using a power source (not shown) to apply a voltage across the main and side balloon electrodes 718m, 718s. For example, the main balloon electrodes 718m may be biased at a first potential, and the side balloon electrodes electrode 718s may be biased at a second potential, which is positive relative to the potential of the main balloon electrodes 718m. Consequently, negatively charged drug within a polymeric coating lying on the outside surface of the main balloon 710m between the main electrodes 718m and the side electrodes 718s will experience an electric field having a direction that urges the charged drug out of the coating and into the plaque 724 lying between the electrodes 718m, 718s. A similar effect may be used to promote transport of drug within a polymeric coating lying on the outside surface of the side balloon 710s. For example, under the same bias conditions (side balloon electrodes 718s having a potential that is positive relative to that of the main balloon electrodes 718m), positively charged drug within the polymeric coating lying on the outside surface of the side balloon 710s between the side electrodes 718s and the main electrodes 718m will experience an electric field having a direction that urges the positively charged drug out of the polymeric coating and into the plaque 724.

Alternatively, both the main balloon 710m and the side balloon 710s may be provided with drugs having the same charge, with the drug being driven from the respective balloons by changing the bias. For example, in the event that a negatively charged drug is selected, biasing the side balloon electrodes 718s to have a potential that is positive relative to that of the main balloon electrodes 718m, will cause negatively charged drug within the polymeric coating lying on the outside surface of the main balloon 710m between the main electrodes 718m and the side electrodes 718s to experience an electric field having a direction that urges the charged drug out of the coating and into the plaque 724. Subsequent to or concurrent with this iontophoresis step, a voltage scheme suitable to cause electroporation may also be applied to enhance cellular delivery. Reversal of the polarity such that the main balloon electrodes 718m have a potential that is positive relative to that of the side balloon electrodes 718s, will then cause negatively charged drug within the polymeric coating lying on the outside surface of the side balloon 710s that is between the side electrodes 718s and the main electrodes 718m to experience an electric field having a direction that urges the charged drug out of the polymeric coating and into the plaque 724. As before, subsequent to or concurrent with this iontophoresis step, a voltage scheme suitable to cause electroporation may also be applied to enhance cellular delivery.

Figure 11:
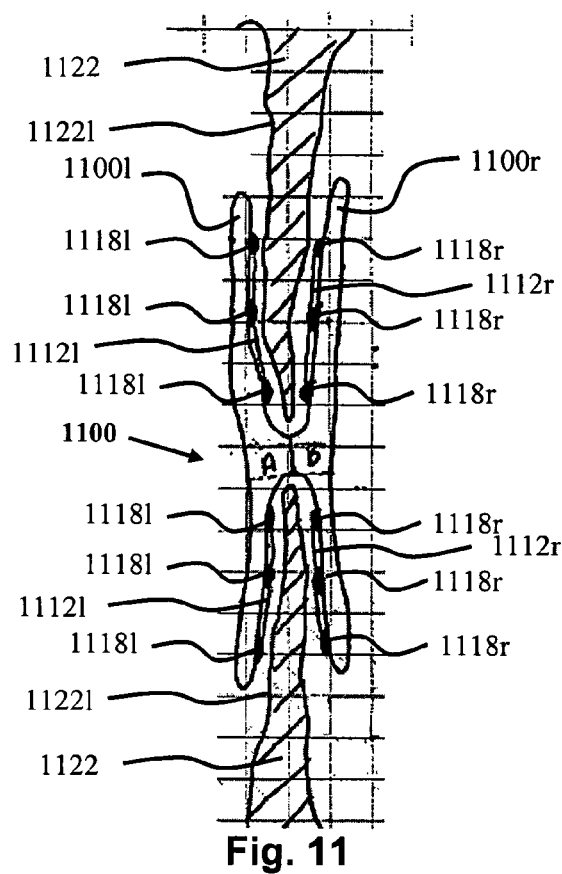
FIG. 11 is a schematic cross-sectional view of an atrial septal defect closure device, disposed at a septal defect, in accordance with an embodiment of the present invention.

Another embodiment of the invention is illustrated in conjunction with FIG. 11. This figure shows an atrial septal defect (ASD) closure device 1100, which includes a left disc 1100l and a right disc 1100r, positioned on either side of a defect in the atrial wall 1122. The left disc 1100l is provided with one or more left electrodes 1118l, which include, for example, a single spiral electrode or a series of concentric electrode rings, among many other designs. The right disc 1100r is provided with one or more right electrodes 1118r, which are typically of the same design of the left electrodes 1118l, although this is not necessarily the case. Disposed over the left and right electrodes 1118l, 1118r, are left and right drug-containing layers 1112l, and 1112r, respectively, which may contain, for example, a charged drug and an ion-conductive polymer.

The left and right discs 1110l, 1110r may be positioned on either side of the atrial wall 1122 using the following technique, among others. This technique may be undertaken under general anesthesia with transesophageal and fluoroscopic guidance. The device 1100 is releasably attached (e.g., by a screw thread) to an elongated member, such as a stiff insulated cable that contains at least two conductors, one in electrical contact with the one or more left electrodes 1118l of the left disc 1100l and the other in electrical contact with the one or more right electrodes 1118r of the right disc 1100r. The left and right discs 1100l, 1100r of the device 1100 are collapsed down and inserted into a sheath (e.g., a catheter), which has previously been advanced from the femoral vein to the left atrium of the heart. The device 1100 is advanced through the sheath by pushing the cable. As the device 1100 emerges from the sheath, the left disc 1100l springs open. The sheath and device 1100 are then pulled back so the left disc 1100l fits snugly against the left atrial wall 1122l. The sheath is then withdrawn further, causing the right disc 1100r to spring open, whereby the device seals the defect in the atrial wall.

A voltage may then be applied between the left and right electrodes 1118l, 1118r such that charged therapeutic is driven via iontophoresis from the left polymeric layer 1112l, the right polymeric layer 1112r, or both, toward the tissue of the atrial wall 1122 that is positioned between the left and right discs 1100l, 1100r. As discussed above, therapeutic agent may be driven from both discs without reversing polarity, where the therapeutic agents in the left and right discs 1100l, 1100r are of opposite charge (and hence migrate toward each other), or by reversing the polarity, where the therapeutic agents are of the same charge. A voltage scheme suitable to cause electroporation may also be applied to enhance delivery, either subsequent to or concurrent with the iontophoresis step(s).

Figure 12:
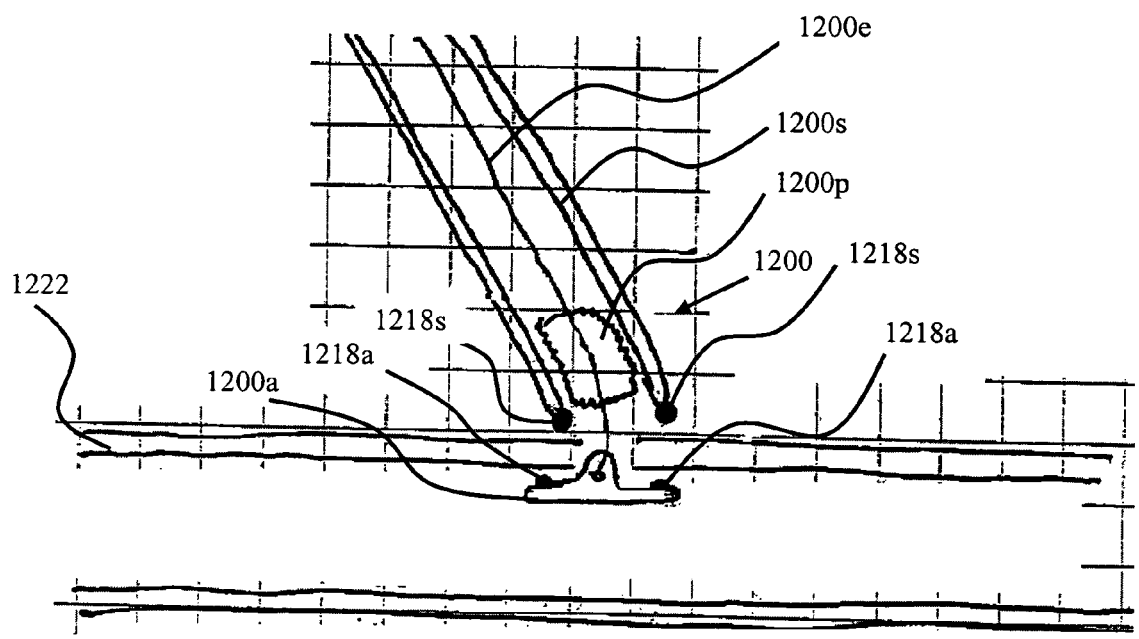
FIG. 12 is a schematic cross-sectional view of a device for sealing an arterial puncture site, disposed at an arterial puncture site, in accordance with an embodiment of the present invention.

Still another embodiment of the invention is shown in FIG. 12, which illustrates a device 1200 for sealing an arterial puncture site (e.g., for sealing a puncture in the femoral artery following cardiac catheterization), among other puncture sites.

The device 1200 provides a mechanical block of a puncture site in an artery 1222 by positioning an anchor 1200a, with an attached suture 1200e, on the interior of the artery 1222. The anchor 1200a and suture 1200e also position and hold a plug 1200p within the puncture (e.g., the tract that is created by the catheterization). The anchor 1200a, suture 1200e and plug 1200p may be formed, at least in part, using a biodegradable material, such as polylactide, polyglycolide, poly(lactide-co-glycolide), collagen, and so forth. The anchor 1200a is further provided with one or more electrodes 1218a (e.g., nonbiodegradable or biodegradable electrodes such as magnesium electrodes), which are preferably covered with one or more drug-containing regions (not separately illustrated), for example, a polymeric region containing a charged drug and an ion-conductive polymer. The one or more electrodes 1218a may be connected to an external power source, for example, via a conductor within suture 1200e. The anchor 1200a is delivered using a delivery sheath 1200s, which further includes one or more electrodes 1218s disposed at or near its distal end and connected to an exterior power source, for example via one or more conductors within the sheath 1200s.

During placement of the device 1200, the sheath 1200s and anchor 1200a, are introduced into the artery 1222. The device 1200 is then withdrawn until the anchor 1200a is seated in the artery puncture. The plug 1200 is then introduced along the suture 1200e through the sheath 1200s until it is positioned at the outer arterial wall 1222. If desired, a tamper may be employed to compress the plug against the outer arterial wall 1222.

At some point prior to withdrawal of the sheath 1200s, a voltage is applied between the sheath and anchor electrodes 1218s, 1218a, such that charged therapeutic is driven via iontophoresis from the polymeric layer on the anchor, toward artery wall 1222 tissue that is positioned between sheath 1200s and anchor 1200a. If desired, an additional charged therapeutic agent may be positioned over the sheath electrodes 1218s and also driven toward the tissue of the artery wall 1222 using techniques such as those discussed above. A voltage scheme suitable to cause electroporation may also be applied to enhance delivery, either subsequent to or concurrent with the iontophoresis step(s). The suture may then be cut and the sheath removed to complete the procedure.

Figure 13:
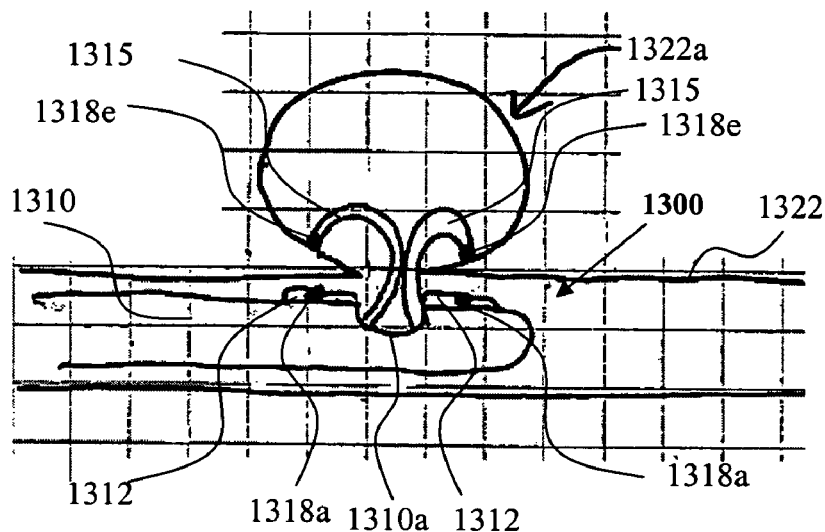
FIG. 13 is a schematic partial cross-sectional view of a device for treating an aneurysm, disposed at an aneurismal site, in accordance with an embodiment of the present invention.

Yet another embodiment of the invention is shown in FIG. 13, which is a schematic partial cross-sectional view of a device 1300 for the treatment of an aneurysm 1322a within a blood vessel wall 1322. The device 1300 includes an elongated catheter 1310 having an aperture 1310a at or near its distal end. One or more electrodes 1318a are provided in the vicinity of the aperture 1310a, for example, encircling the aperture 1310a. Over the electrodes 1318a are provided one or more polymeric coatings 1312, which contain a therapeutic agent, for example, a charged therapeutic agent dispersed within an ion-conductive polymeric coating. The device 1300 further includes one or more extendable members 1315 which are extendable from the aperture 1310a and have one or more electrodes 1318e provided at their distal ends.

During operation, the catheter 1310 is inserted into blood vessel 1322 and advanced until the aperture 1310a is positioned adjacent the aneurysm 1322a within the vessel 1322. The extendable members 1315 are then extended from the aperture 1310a and into the aneurysm 1322a. The extendable members 1315 are provided with a mechanical memory such that they curl upon entering the aneurysm, positioning the electrodes 1318e adjacent the aneurysmal opening. A voltage is applied between electrodes 1318a and electrodes 1318e such that charged therapeutic is driven via iontophoresis from the polymeric layer 1312 toward the aneurysmal opening and the tissue surrounding the same. If desired, an additional charged therapeutic agent may be positioned over the electrodes 1318e and also driven toward the aneurysmal opening and the tissue surrounding the same from the opposite side. A voltage scheme suitable to cause electroporation may also be applied to enhance delivery, either subsequent to or concurrent with iontophoresis.

In other related embodiments, a metal aneurysmal coil, such as a GDC coil may be used as the electrode within the aneurysm to provide a similar effect.

Other embodiments of the invention are directed to implantable cardioverter defibrillators (ICDs), which comprises a pulse generator connected to one or more electrodes for sensing and pacing, and one or more electrodes for defibrillation by delivering high-voltage shocks to the heart.

In many systems, the pulse generator can serve as a part of the defibrillation pathway. For example, the shell of the pulse generator may be conductive and thus act as the defibrillation anode and a single coil may act as the defibrillation cathode. Such single coil devices also commonly have tip and ring electrodes, which act as bipolar electrodes for sensing and pacing. Because both pacing/sensing electrodes are independent of the defibrillation coil, they form what is called a dedicated bipole.

In other systems, known as dual-coil devices, distal (cathode) and proximal (anode) defibrillation coils are provided. The shell of the pulse generator can also serve as an additional anode for the device, if desired. A single tip electrode is also commonly provided in such devices, with the distal coil being integrated into the pacing and sensing functions as well. Because the defibrillation coil is linked to the electrode for sensing/pacing, it forms what is called an integrated bipole.

Electrode placement within a patient may vary. Taking one placement scheme for a dual coil device as an example, a lead containing the two defibrillation coils and tip electrode may be advanced into the heart, for example, to the point where (a) the tip electrode resides in the right ventricular apex (e.g., wedged into the trabeculae), (b) the distal defibrillation coil resides in the right ventricle, and (c) the proximal defibrillation coil resides in the superior vena cava. For a single coil device, on the other hand, the tip electrode may again reside in the right ventricular apex while the defibrillation coil may reside in the right ventricle.

Of course many other designs and electrode placements are possible. For example, dual-chamber and biventricular devices are also known, which have ports for atrial or left ventricular electrodes that are used for pacing and sensing.

Regardless of the system selected, the defibrillation coils are commonly provided with sleeves to prevent tissue damage. In certain embodiments of the present invention, the coils are coated with one or more polymeric regions, which comprise a charged therapeutic agent and an ion-conductive polymer or a electrically conductive polymer.

Where an electrically conductive polymer is selected, the device is initially inserted into the patient with the conductive polymer in charged (i.e., oxidized or reduced) form, loaded with a therapeutic agent of opposite charge. Upon application of an appropriate voltage, the polymer is converted to a less charged (i.e., more neutral) form, whereupon at least a portion of the charged therapeutic agent is expelled. This voltage may be applied, for example, concurrently with defibrillation, or an appropriate bias may be applied to the polymer coated coil immediately prior to defibrillation, which is sufficient to convert the polymer to a more neutral form. For example, a bias may be applied between the polymer coated defibrillation coil and another defibrillation coil, between the polymer coated defibrillation coil and a separate dedicated or non-dedicated electrode, between the polymer coated defibrillation coil and the shell of the pulse generator, and so forth. In any event, the defibrillation voltages selected are sufficient to cause electroporation of nearby tissue after therapeutic agent release, enhancing delivery of the therapeutic agent.

Where an ion-conductive polymer is selected, the device is also inserted into the patient, loaded with a charged therapeutic agent. Upon application of an appropriate voltage, the charged drug migrates from the polymeric coating in the presence of the resulting electrical field. As above, voltage may be applied, for example, concurrent with defibrillation, or an appropriate bias may be applied to the polymer coated coil immediately prior to defibrillation to expel at least a portion of the therapeutic agent. Also as above, the defibrillation voltages selected are sufficient to cause electroporation of nearby tissue after therapeutic agent release, enhancing delivery of the therapeutic agent.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An internal medical device comprising: (a) electrodes that are adapted to be positioned in a lumen of the cardiovascular system that is created by surrounding tissue upon implantation or insertion of said medical device in a subject, said electrodes further being adapted to have said surrounding tissue positioned between them upon deployment of said medical device within said lumen, (b) a power source adapted to apply a voltage across said electrodes, thereby generating an electric field having a vector that is directed into said surrounding tissue, and (c) a therapeutic agent source adapted to introduce a therapeutic agent into said electric field, wherein said device comprises an expandable tubular medical device substrate, wherein said therapeutic agent source comprises a charged therapeutic agent dispersed within an ion-conductive polymeric coating region disposed over said substrate, and wherein said electrodes comprise a first electrode provided beneath and in electrical contact with the polymeric coating region and a tissue penetrating electrode which penetrates said surrounding tissue upon deployment of said device by expansion of said substrate.

2. The internal medical device of claim 1, wherein said medical device is selected from catheters, grafts, stents, balloons, chronic total occlusion devices, aneurysm treatment devices, angioplasty devices, and filters.

3. The internal medical device of claim 1, wherein said medical device is selected from medical devices that provide new or enhanced paths for flow of bodily fluids subsequent to implantation or insertion and medical devices that obstruct flow of bodily fluids subsequent to implantation or insertion.

4. The internal medical device of claim 1, wherein said power source is adapted to apply a voltage that is sufficient to cause electroporation within said surrounding tissue.

5. The internal medical device of claim 1, wherein said device comprises a plurality of said tissue penetrating electrodes.

6. The internal medical device of claim 5, wherein said plurality of tissue penetrating electrodes are selected from blades, needles and a combination thereof.

7. The internal medical device of claim 6, wherein said needles are selected from metal microneedles, metal alloy microneedles, conductive nanotubes, conductive nanowires, and combinations of the same.

8. The internal medical device of claim 6, wherein said plurality of tissue penetrating electrodes are disposed at an outer surface of said expandable device such that said electrodes pierce said surrounding tissue upon deployment.

9. The internal medical device of claim 1, wherein said power source is adapted to apply a voltage that is sufficient to cause enhanced retention of said charged therapeutic agent, enhanced delivery of said charged therapeutic agent, or both.

10. The internal medical device of claim 9, wherein said power source is further adapted to apply a voltage that is sufficient to cause electroporation within said surrounding tissue.

11. The internal medical device of claim 1, wherein said medical device comprises a plurality of said polymeric coating regions.

12. The internal medical device of claim 11, wherein said medical device comprises a first polymeric coating region that comprises a first charged therapeutic agent having a positive charge and a second polymeric coating region that comprises a second charged therapeutic agent having a negative charge.

13. The internal medical device of claim 1, wherein said polymeric coating region comprises a polymer selected from a polyether, a polyelectrolyte, an electrically conductive polymer, and a combination thereof.

14. The internal medical device of claim 1, wherein said polymeric coating region comprises a polymer selected from a homopolymer, a random copolymer, a periodic copolymer, a block copolymer and a combination thereof.

15. The internal medical device of claim 1, wherein said charged therapeutic agent is selected from a therapeutic agent that is inherently charged, a therapeutic agent that is covalently attached to a charged molecule, a therapeutic agent that is non-covalently attached to a charged molecule, a therapeutic agent that is attached to or encapsulated within a charged particle, and a combination thereof.

16. The internal medical device of claim 1, wherein said charged therapeutic agent comprises charged paclitaxel.

17. The internal medical device of claim 1, wherein said charged therapeutic agent comprises a polyelectrolyte chain.

18. The internal medical device of claim 1, wherein said polymeric coating region is disposed over a polymeric substrate.

19. The internal medical device of claim 18, wherein said polymeric substrate comprises a first polymer comprising a polyether chain, wherein said polymeric coating region comprises a second polymer comprising a polyether chain, and wherein said first and second polymers may be the same or different.

20. The internal medical device of claim 18, wherein said polymeric substrate comprises a first polymer comprising a polyamide chain, wherein said polymeric coating region comprises a second polymer comprising a polyamide chain, and wherein said first and second polymers may be the same or different.

21. The internal medical device of claim 18, wherein said polymeric substrate comprises a block copolymer that comprises polyether and polyamide chains, and wherein said polymeric coating region comprises an ion-conductive polymer that comprises a chain selected from a polyether chain, a polyamide chain, and a combination thereof.

22. The internal medical device of claim 21, wherein said block copolymer comprises polytetramethylene oxide and nylon 12 chains.

23. The internal medical device of claim 22, wherein said ion-conductive polymer comprises a chain selected from a poly(ethylene oxide) chain, a poly(amino acid) polyelectrolyte chain, and a combination thereof.

24. The internal medical device of claim 1, wherein said polymeric region is an ion-conductive polymeric region that comprises an inorganic phase.

25. The internal medical device of claim 1, wherein said polymeric region is an ion-conductive polymeric region that comprises an ionic liquid.

26. The internal medical device of claim 1, wherein said polymeric coating region comprises an electrically conductive polymer and wherein said power source is adapted to apply a voltage that is sufficient to cause electroporation in tissue adjacent to said device.

27. The internal medical device of claim 26, wherein said polymeric coating region comprises a conductive polymer selected from polypyrrole and its derivatives, polyaniline and its derivatives, polythiophene and its derivatives, poly(p-phenylene vinylene) and its derivatives, polysulfone and its derivatives, polyacetylene and its derivatives, and combinations thereof.

28. The internal medical device of claim 26, wherein said polymeric coating region comprises substituted polypyrrole, unsubstituted polypyrrole, or a combination thereof.

29. The internal medical device of claim 26, wherein said device is selected from catheters, grafts, stents, balloons, chronic total occlusion devices, aneurysm treatment devices, filters, and angioplasty devices.

30. The internal medical device of claim 26, wherein said medical device is selected from medical devices that provide new or enhanced paths for flow of bodily fluids subsequent to implantation or insertion and medical devices that obstruct flow of bodily fluids subsequent to implantation or insertion.

31. The internal medical device of claim 26, wherein said polymeric coating region is disposed over a polymeric substrate.

32. The internal medical device of claim 31, wherein said polymeric substrate comprises a block copolymer that comprises polyether and polyamide chains, and wherein said polymeric region comprises substituted polypyrrole, unsubstituted polypyrrole, or a combination thereof.

33. The internal medical device of claim 31, wherein said polymeric substrate is a balloon.

34. The internal medical device of claim 1, wherein sides of said tissue penetrating electrode are provided with a layer of insulating material.

35. The internal medical device of claim 1, wherein the tissue penetrating electrode is in the form of a needle.

36. The internal medical device of claim 1, wherein the tissue penetrating electrode is in the form of a blade.

37. The internal medical device of claim 1, wherein the expandable tubular medical device substrate is a balloon.

38. the medical device of claim 26, wherein said conductive polymer has a conjugated backbone.

39. The medical device of claim 1, wherein said body lumen is an artery lumen.

40. The internal medical device of claim 6, wherein said needles are conductive carbon nanotubes.

41. The internal medical device of claim 26, wherein said conductive polymer is an overoxidized conductive polymer.

42. The internal medical device of claim 41, wherein said overoxidized conductive polymer is overoxidized polypyrrole.

* * * * *